United States Patent [19]

Ranney

[11] Patent Number: 5,213,788
[45] Date of Patent: May 25, 1993

[54] PHYSICALLY AND CHEMICALLY STABILIZED POLYATOMIC CLUSTERS FOR MAGNETIC RESONANCE IMAGE AND SPECTRAL ENHANCEMENT

[76] Inventor: David F. Ranney, 3539 Courtdale Dr., Dallas, Tex. 75234

[21] Appl. No.: 680,675

[22] Filed: Apr. 4, 1991

Related U.S. Application Data

[63] Continuation-in-part of Ser. No. 463,692, Jan. 11, 1990, which is a continuation-in-part of Ser. No. 252,565, Sep. 29, 1988, abandoned.

[51] Int. Cl.$^5$ .................. G01N 24/08; C07H 23/00; A61K 33/24; A61K 31/725
[52] U.S. Cl. .................................. 424/9; 424/4; 424/617; 514/56; 514/836; 436/173; 436/806; 128/653.4
[58] Field of Search ............... 424/4, 9, 2, 617; 436/173, 806; 128/653 AF, 653 CA, 654; 514/56, 836

[56] References Cited

U.S. PATENT DOCUMENTS

| | | | |
|---|---|---|---|
| 4,247,406 | 1/1981 | Widder et al. | 252/62.53 |
| 4,370,476 | 1/1983 | Usher | 536/113 |
| 4,385,046 | 5/1983 | Milbrath et al. | 424/1.1 |
| 4,423,158 | 12/1983 | Porath | 521/32 |
| 4,452,773 | 6/1984 | Molday | 424/1.1 |
| 4,472,509 | 9/1984 | Gansow | 436/548 |
| 4,639,365 | 1/1987 | Sherry | 424/9 |
| 4,647,447 | 3/1987 | Gries et al. | 424/9 |
| 4,731,239 | 3/1988 | Gordon | 424/9 |
| 4,735,210 | 4/1988 | Goldenberg | 424/4 |
| 4,735,796 | 4/1988 | Gordon | 424/9 |
| 4,770,183 | 9/1988 | Groman et al. | 128/654 |
| 4,822,594 | 4/1989 | Gibby | 424/9 |
| 4,832,877 | 5/1989 | Bino et al. | 260/414 |
| 4,904,479 | 2/1990 | Illum | 424/490 |
| 4,957,939 | 9/1990 | Gries et al. | 514/492 |
| 4,963,344 | 10/1990 | Gries et al. | 424/9 |
| 4,985,233 | 1/1991 | Klaveness et al. | 424/9 |
| 4,986,980 | 1/1991 | Jacobsen | 424/9 |
| 5,021,236 | 6/1991 | Grieset et al. | 424/9 |
| 5,055,288 | 10/1991 | Lewis et al. | 424/9 |

FOREIGN PATENT DOCUMENTS

| | | |
|---|---|---|
| 0184899A1 | 6/1986 | European Pat. Off. |
| 0186947 | 7/1986 | European Pat. Off. |
| WO 85/05554 | 12/1985 | PCT Int'l Appl. |
| 1529150 | 9/1977 | United Kingdom |
| 2137612 | 10/1984 | United Kingdom |

OTHER PUBLICATIONS

Geraldes et al., "Magnetic Field Dependence of Solvent Proton Relaxation Rates Induced by $Gd^{3+}$ Complexes of Various Polyaza Macrocyclic Ligands: Implications for NMR Imaging," *Magnetic Resonance in Medicine*, 3:242–50 (1986).

(List continued on next page.)

*Primary Examiner*—Richard L. Raymond
*Assistant Examiner*—Gary E. Hollinden
*Attorney, Agent, or Firm*—Arnold, White & Durkee

[57] ABSTRACT

Improved compositions and methods for selective access to tumor regions (or other regions of abnormal endothelial properties). This capability provides powerful contrast-enhancement agents for nuclear magnetic resonance imaging. A polyatomic complex which includes intramolecular ferromagnetic coupling between metal atoms is associated with a polymer or microsphere carrier matrix which will bind to endothelial determinants. A solution containing this carrier complex is injected into a human (or other) body to be imaged. The carrier complex will preferentially extravasate at locations where the blood vessel walls have increased porosity or microvascular surface changes, and especially at tumor sites. Thus, the changes in relaxation time induced by the presence of the carrier complex will provide a high-gain marker for magnetic resonance imaging.

Multiple superparamagnetic polyatomic complexes are described, including novel complexes which include acetate and glycinate bridging ligands with a polyatomic metal-atom-complex core.

40 Claims, 12 Drawing Sheets

OTHER PUBLICATION

Goldstein et al., "Gadolinium DTPA (An NMR Proton Imaging Contrast Agent): Chemical Structure, Paramagnetic Properties and Pharmacokinetics," *Physiol. Chem. & Phys. & Med. NMR,* 16:97–104 (1984).

Wolf, "Contrast Enhancement in Biomedical NMR," *Physiol. Chem. & Phys. & Med. NMR,* 16:93–95 (1984).

Sherry, "Lanthanide Chelates as Magnetic Resonance Imaging Contrast Agents," *J. Less Common Metals,* 149:133–141 (1989).

Lauffer, R. and Brady, T., "Preparation and Water Relaxation Properties of Proteins Labeled with Paramagnetic Metal Chelates," *Mag. Res. Imag.* 3:11–16 (1985).

Bino et al., "[$Cr_4S(O_2CCH_3)_8(H_2O)_4$]($BF_4$)$_2$.$H_2O$: Ferromagnetically Coupled $Cr_4S$ Cluster with SPIN 6 Ground State", *Science,* 241:1479–1481 (1988).

Bulman et al., "Investigations into Techniques for Removing Intracellular Plutonium—II. Complexing Agents Bound to Macromolecules," *Health Physics* 40:228–231 (1980).

Martell, A., "The Design and Synthesis of Chelating Agents," *Development of Iron Chelators for Clinical Use* pp. 67–104 (1981).

Dawson, et al., "Progress Toward the Synthesis of Polymerically Bound Chelating Agents for Iron (III) and the Development of a New Assay Method for Determining Iron Chelator Effectiveness," *Development of Iron Chelators for Clinical Use,* pp. 201–209 (1981).

Lauffer, et al., "Iron-EHPG as an Hepatobiliary MR Contrast Agent: Initial Imaging and Biodistribution Studies," *Proc. Soc. Mag. Resonance in Med.,* pp. 883–884 (Aug. 1985).

Lauffer et al., "Preparation and Water Relaxation Properties of Proteins Labeled with Paramagnetic Metal Chelates," *Magnetic Resonance Imaging* 3:11–16 (1985).

Chan et al., "ESR Study of the Interaction Between Macrophages and Liposomes Containing Spin Labels as NMR Contrast Agents," *Proc. Soc. Mag. Resonance in Med.,* pp. 846–847 (Aug. 1985).

Buonocore, et al., "Potential Organ Specific MRI Contrast Agents for Liver and Spleen: Gadolinium Labeled Liposomes," *Proc. Soc. Mag. Resonance in Med.,* pp. 838–839 (1985).

Widder et al., "Magnetically Responsive Microspheres as a Carrier by Site-Specific Delivery of Adriamycin", *Proc. Am. Assoc. Cancer Res.* 19:17, (Mar. 1978).

Blank et al., "Liposomal Encapsulated An-DTPA for Removing Intracellular YB," *Health Physics,* 39:913–920 (1980).

Erichsen et al., "Blockage of the Hepatic-Artery Blood Flow by Biodegradable Microspheres (Spherex ®) Combined with Local Hyperthermia in the Treatment of Experimental Liver Tumors in Rats," *J. Cancer Res. Clin. Oncol.* 109:38–41 (1985).

Brasch et al., "Contrast-Enhanced NMR Imaging: Animal Studies Using Gadolinium-DTPA Complex," *AJR* 142:625–630 (Mar. 1984).

Weinman et al., "Characteristics of Gadolinium-DTPA Complex: A Potential NMR Contrast Agent," *AJR* 142:619–624 (Mar. 1984).

Burnett et al., "Gadolinium Oxide: A Prototype Agent for Contrast Enhanced Imaging of the Liver and Spleen with Magnetic Resonance," *Magnetic Resonance Imaging,* 3:65–71 (1985).

Chen et al., "Paramagnetic Metalloporphyrins as Potential Contrast Agents in NMR Imaging," *FEBS Letters* 1274, vol. 168, No. 1:70–74 (1984).

Desreux, J., "Nuclear Magnetic Resonance Spectroscopy of Lanthanide Complexes with a Tetraacetic Tetraaza Macrocycle Unusual Conformation Properties," *Inorg. Chem.* 19:1319–1324 (1980).

Kienle et al., "The Polyhydric Alcohol-Polybasic Acid Reaction. III. Further Studies of the Glycerol-Phthalic Anhydride Reaction," *J. Am. Chem. Soc.* 61:2258 (1939).

PCT International Search Report for International Appln. No. PCT/US/86/02479 (1986).

Runge, et al., "Work in Progress: Potential Oral and Intravenous Paramagnetic NMR Contrast Agents," *Radiology* 147:789–791, (Jun. 1983).

Dorland's Illustrated Medical Dictionary Twenty-Sixth Edition p. 325 (1985).

PHYSICALLY AND CHEMICALLY STABILIZED POLYATOMIC CLUSTERS FOR MAGNETIC RESONANCE IMAGE AND SPECTRAL ENHANCEMENT

This is a continuation-in-part of U.S. Ser. No. 463,692, filed Sept. 29, 1989, is a continuation-in-part of U.S. Ser. No. 252,565 filed Jan. 11, 1990 abandoned which are incorporated by reference herein.

The present application relates to formulations of polyatomic clusters which are rendered useful for in vivo magnetic resonance imaging (MRI) and spectral enhancement by means of physical, chemical, and combined physical-chemical stabilization. Said clusters are defined as polyatomic molecular complexes containing multiple atoms of either the same or of different atomic number, wherein two or more of the atoms have a magnetic moment. In selected cases, the polyatomic cluster may cause the atoms of magnetic moment to be oriented in ferromagnetic alignment, such that their multiple magnetic moments are additive intramolecularly, thereby giving the cluster a total magnetic moment greater than that of any individual atom of magnetic moment. Said polyatomic clusters may contain single or plural bridging ligands (for the purposes of this disclosure the term "bridging ligand" is equivalent to the term "bridging molecular or atomic species"), however, such bridging ligands may be distinguished from classical chelators, in that the bridging ligands, when plural, are not covalently linked together to form multiple covalent coordination sites.

Stabilization of said polyatomic clusters by the present compositions and methods of formulation results in favorable potency, plasma stability, biodistribution, delivery to desired target sites, excretion, toxicity, and/or other favorable in vivo properties, in comparison to parallel properties of the native polyatomic clusters alone. Said polyatomic cluster formulations include, but are not limited to clusters which are chemically or physically associated with carrier substances. Carrier substances are defined as substances with which the polyatomic clusters are chemically or physically associated for the purpose of altering the in vivo properties described above. In this context, such carrier substances are distinguished from existing, traditional formulation carriers and pharmaceutical vehicles, in that these existing, traditional substances are used principally to render diagnostic agents in optimal states for solubilization, processing, drying or other aspects of in vitro formulation.

Association and stabilization of the present polyatomic clusters with carrier substances may be by physical, chemical or combined physical-chemical means. Chemical means may include, but are not limited to binding of said clusters to carrier substances by hydrophobic bonding, hydrogen bonding, paired-ion association, multiple paired-ion association, and partial or total coordination or trans-chelation binding of the polyatomic clusters to the carrier substances via single or multiple ligands which are themselves bound to these carrier substances. In the case of coordination or trans-chelation binding of polyatomic clusters to carrier substances, it is important to note that such coordination or trans-chelation is explicitly for the purpose of intermolecular attachment of the polyatomic cluster to the carrier substance, and not for the purpose of intramolecular stabilization of the polyatomic cluster. Hence, although partial chelation of the polyatomic cluster may result as a byproduct of carrier binding, the polyatomic cluster is considered to remain as such and not to change into a classical (full) chelate by virtue of this mechanism of carrier binding.

The formulations used for physical and combined physical-chemical stabilization typically include one or more of: emulsification, dispersion stabilization, low or high pressure homogenization, sonification, heat stabilization, other energy-input processes, organic solvent processing, aqueous solvent processing, combined organic-aqueous cosolvent processing, cosolvent processing wherein one or more of the cosolvents is a nonsolvent or partial nonsolvent for the polyatomic cluster or the carrier substance or both, and other forms of chemical stabilization or binding.

Magnetic resonance images (MRI) have been obtained from the brain and body of living animals and humans by means of applying pulsed radio frequency (rf) energy in the presence of strong fixed and gradient magnetic fields, and monitoring the induced signals given off by atoms and ions with a magnetic moment and characteristic frequency of nuclear oscillation in the defined strong magnetic field. One major advantage of MRI images, in relation to other medical imaging modalities, is that they provide an important means of clinical brain and body imaging of internal structures, organs and foci of disease typically at a very high spatial resolution of less than about $0.3 \times 0.3$ mm inplane resolution and 2 mm slice thickness.

MRI image enhancement has been accomplished successfully in vivo by producing alterations in the relaxation times and/or spectral shifts of paramagnetic atoms present in the animal or human being imaged. Such enhancements (spectral shifts) have been produced by administering, among others, the following major classes and examples of MRI diagnostic agents:

1. paramagnetic ions and chelates, such as gadolinium diethylenetriamine pentaacetic acid dimeglumine (Gd—DTPA dimeglumine—Berlex-Schering AG; West Germany patent filed by Gries, Rosenberg and Weinman: DE-OS 3129906 A 1 (1981)), and gadolinium DOTA;
2. superparamagnetic substances, such as dextran iron;
3. ferromagnetic substances, such as micronized iron; and
4. polyatomic molecular clusters, including:
   a. (1) homopolyatomic clusters, including the CrIII cluster, $[Cr_4S(O_2CCH_3)_8(H_2O)_4]^{2+}$ (A Bino, et al, U.S. Pat. No. 4,832,877, issued May 23, 1989; and A Bino, et al, Science, Sept. 16, 1988); and
   a. (2) heteropolyatomic clusters.

In clinical imaging, these substances typically produce enhancement by altering the T1 or T2 relaxation times (or shifting the spectra) of induced magnetic signals given off by paramagnetic atoms present in the body, usually comprising water and fat protons and less commonly including carbon and phosphorous nuclei, but potentially including exogenously administered magnetic ions and atoms such as $^{19}$fluorine. Paramagnetics typically act as T1-weighted enhancing agents. Superparamagnetics and ferromagnetics typically act as T2-weighted enhancing agents. Polyatomic clusters may act as either T1- or T2-weighted agents depending on their size; the orientation of their intramolecular component atomic magnetic moments; and the activity or cancellation of intermolecular magnetic moments, which may be influenced by various super-molecular formulation states.

The major difficulties encountered in discovering and formulating previous MRI image enhancing (spectral shift) agents are as follows:

1. these agents are typically quite toxic in their free ionic form—particularly for the currently favored, paramagnetic ion, gadolinium, which is the most potent ion available for paramagnetic relaxation due to its maximal number of seven unpaired electrons;
2. the free agents are typically water insoluble or very poorly water soluble at physiologic pH;
3. the agents must be administered in relatively high doses due to the inherent insensitivity of MRI imaging;
4. after chelation of the existing paramagnetic agents, which is required to confer acceptable water solubility, toxicity and body clearance, these agents:
   a. lose a significant fraction of their potency because the chelator's functional groups occupy almost all of the paramagnetic ion's inner coordination sites coinciding with the strongest portion of the ion's paramagnetic dipole; and
   b. act as nonselective (nonspecific) contrast agents due to their rapid free diffusion into normal extracellular body fluid, as well as into sites of disease (Note: in the brain but not the body, such diffusion into the normal extracellular fluid is reduced but not entirely eliminated by the presence of a blood-brain barrier);
5. due to their rapid free diffusion in body water, previous paramagnetic-ion chelates:
   a. typically fail to enhance the very small lesions (sites of disease less than 5 mm in diameter), which are theoretically capable of resolution by current MRI instrumentation technology;
   b. fail to optimally discriminate between perfused and nonperfused subregions of tumor nodules and localized infections, due to the their even more rapid diffusion through the less structured (bound) interstitial water (extracellular tissue compartment) within these sites of disease; and
   c. backdiffuse very rapidly from these sites of disease into the bloodstream, thereby minimizing the time available for image acquisition after intravenous administration of these contrast agents (typically to less than 15-30 minutes), thereby eliminating the possibility of pre-dosing patients outside the imaging room.
6. existing superparamagnetic and ferromagnetic agents:
   a. require a relatively long time for total body clearance (typically several days to weeks), thereby presenting substantial regulatory disadvantages; and
   b. act predominantly as T2-weighted agents, which typically darken rather than brighten (enhance) MRI images of the tissues and sites in which these agents become localized.
7. existing paramagnetic, superparamagnetic and ferromagnetic agents are either ineffective or markedly suboptimal for MRI blood-pool and perfusion image contrast enhancement.

It has previously been shown by the present applicant, as disclosed in previous filings (International Applications PCT/US88/01096, PCT/US89/04295, that selectivity of uptake at sites of disease could be achieved for MRI contrast agents by simultaneously employing both of the mechanisms described in Nos. 1. and 2. (immediately below):

1. Covalent or noncovalent association of magnetic agents with carrier substances which confer sufficient size—at least about 15,000 to 20,000 MW—to exclude rapid, free exchange of diagnostic agents between the blood compartment and the extracellular fluid compartment (interstitium) of normal body tissues; and
2. Covalent and noncovalent association of magnetic agents with carrier substances which bind selectively to determinants induced on the endothelium (and epithelium) at sites of disease; and normally present on the endothelium of certain organs (e.g., lung among others). Such binding, in turn, induces active uptake of the agent-carrier combination across these intermediate barrier structures (endothelium and epithelium) into the interstitial compartment of the diseased tissues (lesional sites) and in certain cases, normal target organs. For particular carrier substances, including but not limited to heparins and heparan sulfates, such selective, active lesional uptake has also been shown to be accompanied by prolonged lesional retention of the diagnostic-carrier (or drug-carrier) combination. This is due theoretically to binding of heparins (and other related, usually negatively charged carbohydrates and glycoaminoglycans) to endogenous heparan sulfates and related binding substituents which become induced or exposed within the interstitial compartment of tumors, infections, tissues altered by various inflammatory conditions and other lesional sites, particularly those involving vascular and/or tissue remodeling as a component of the disease.

Among the novel teachings set forth in the present application is the recent unpublished data obtained by the present applicant, which indicate that the active uptake of heparin, and potentially other negatively charged carbohydrates and related molecules, occurs selectively at lesional sites even below the applicants' and others' previously published size-exclusion cutoff of 15,000 to 20,000 Daltons, and hence, occurs even in the absence of the size exclusion mechanism described in immediately above. This affords a significantly improved basis for site-selective uptake of carrier-associated diagnostic (and therapeutic) agents in tumors and other lesional sites. It also provides a new basis for constructing novel, selective MRI contrast agents, including polyatomic cluster-carrier compositions, at a size substantially less than the approximately 15,000 MW cutoff at which size exclusion prevents their rapid, free exchange into normal body tissues. Such novel MRI contrast agents have multiple advantages, including:

1. the most rapid plasma clearance available for any site-selective agent described to date (t ½ of less than about 30 minutes, which very nearly equals the t ½'s of 20 minutes characteristic of nonselective agents), producing reduced background enhancement from plasma and para-lesional sites at early postinjection imaging times;
2. improved lesional access and prolonged lesional-site retention (of up to several hours);
3. essentially complete avoidance of uptake by normal liver, producing maximal lesional-to-normal organ enhancement ratios for hepatic tumors and other focal liver diseases;
4. more rapid and complete body clearance, which occurs almost exclusively by the renal route;
5. minimization of carrier side effects, which results from utilization of the lowest molecular weight fractions of heparin (e.g., ca. 8,000 mean MW) commercially available in large quantity at acceptable cost;
6. capability to use the heparin fractions and sources which have optimal sulfation ratios for both:
   a. multiple paired-ion binding of cationic MRI polyatomic complexes; and
   b. optimal complementarity to and interaction with the endothelial (and epithelial) determinants, including heparan sulfates, which appear to be responsible for lesional site selectivity.
7. optimal reformulation into extremely small, round, physically stabilized nanospheres (see below).

Also among the novel teachings set forth in the present application is reformulation of the preceding soluble MRI-carrier combinations in such a fashion as to provide new, extremely small nanospheres, typically less than the 100 nanometer diameter mean size previously disclosed by the applicant (PCT/US89/04295), and preferably about 5-99 nanometers in diameter. Such very small nanospheres confer, among others, the following major advantages:
1. the most rapid uptake of particles available from the blood plasma across endothelial (and epithelial) barriers into sequestered tissue sites and sites of disease, via "rapid" transport vesicles, at a rate which markedly exceeds that of larger particles with diameters greater than about 100–120 nanometers;
2. the most complete bioavailability possible of entrapped magnetic agents, against which water protons need to diffuse with minimal obstruction in order to afford maximal MRI relaxivity and in vivo potency per unit of entrapped magnetic species;
3. when desired (see below), optimal delayed dissociation of the entrapped diagnostic agents from the carrier substances, leading to rapid body clearance and maximizing the fraction o diagnostic agent which clears by the renal route.

Also among the novel teachings set forth in the present application is the reformulation of the preceding soluble MRI agent-carrier combinations, which incorporate low molecular weight heparin fractions of about 8,000 mean MW, into single-component and mixed-component, nanospheres of about 5–99 nanometers (mean diameter) as well as larger microspheres of about 0.1 to 250 um in mean diameter, to form:
1. agent-heparin microspheres with rapid bioavailability of entrapped MRI agent (or other actives), together with optimal spherical shape (in comparison to microspheres formulated with higher MW heparins in the mean MW range of about 16,000 to 22,000 Daltons).
2. mixed-component nanospheres and microspheres containing the magnetic agent entrapped in both heparin and protamine, hexadimethrine or starch matrix components, among others which range respectively and reciprocally from about 2 to 98 weight ratios, and wherein the second matrix component confers additional microsphere stability, as well as potentially (depending in part on diameter) extended or less commonly, accelerated release of the entrapped agent.

Also among the novel teachings of [those] set forth in the present application is that formulation of these presently described nanoparticles and microparticles using the newly described lower-molecular weight heparin fractions, causes these particulate reformulations to have improved lesional-site and organ-site selectivity, and can confer other advantageous properties of these novel nanoparticles and microparticles within the animal or human being imaged.

Examples of optimal heparins include but are not limited to the more heavily sulfated, Fraction A heparins, and especially preferably those Fraction A heparins derived from beef-lung source. These heparins have not only improved sulfation ratios in vitro, but also improved complementarity to and interaction with endothelia (and epithelia) in vivo, as evidenced by improved in vivo binding to endothelium (and epithelium) and resultant site localization (see Examples). Such heparins classically include, and are herein further defined as including, various low molecular weight and rapidly eluting chromatographic fractions of heparins, such as those with a mean molecular weight of about 8,000 Daltons, those with a molecular weight range of about 6,000 to 10,000 Daltons, and fragments of those heparins which may range from about 1,000 Daltons to about 10,000 Daltons. Furthermore, such heparins may also be obtained from sources other than beef-lung, including but not limited to porcine mucosa, other animal species and organ sources, and from genetically engineered (recombinant DNA) prokaryotic or eukaryotic fermentation or cellular systems, among others. The heparins just described confer novel advantages, including in vivo site uptake and site selectivity for the soluble as well as the particulate, novel formulations described in the present application. Importantly, this subgroup of heparins provides such advantages even in the absence of the larger molecular size ranges of about 15,000 to 22,000 Daltons, previously thought to be necessary for prevention of free diffusion into normal tissues based on the mechanisms of size exclusion across capillary endothelial (and epithelial) barriers.

The size of both nanoparticles and microparticles are supramolecular. As taught in the present application, the optimal mean size of nanoparticles is less than about 100 nm in 10 diameter, with the preferred mean diameter falling between about 5 and 99 nanometers. This is because "rapid" endothelial transport vesicles, whose activity is required for the very most rapid, selective transport of MRI enhancing agents from the blood (plasma) across microvascular endothelial barriers into the tissues, provide maximal transport rates and efficiencies for nanoparticles less than about 100 to 120 nanometers in diameter. Secondly, nanoparticles of less than about 100 nanometers in diameter allow the maximal quantity of entrapped magnetic agent to be made available rapidly to surrounding, diffusible magnetic atoms and molecules within body tissues. Thirdly, nanoparticles of this small size appear optimal for blood-pool image enhancement. It should be noted in this regard, that larger microparticles of 0.1 to 250 micrometers in diameter may also be formulated to undergo timely dissolution, such that essentially all of their entrapped magnetic material is also made available for interaction at pertinene distances of less than about 10 angstroms with surrounding diffusible magnetic species. Still, for formulations containing the same carrier (particle matrix) materials, the smaller nanoparticles typically dissolve more rapidly than do the larger microparticles.

Previous publications have disclosed entrapment of gadolinium chelates, such as gadolinium diethylenetriamine pentaacetic acid (Gd-DTPA), in relatively small liposomes, in order to selectively enhance MRI images of the reticuloendothelial organs (liver, spleen and bone marrow) and potentially the lungs. (Buonocore et al., 2 *Proc. Soc. Mag. Res. Med.* 838 (1985)(which is hereby incorporated by reference).) Liver clearance is mediated by phagocytic (Kupffer) cells which spontaneously remove these small (0.05 to 0.1 micron) particles from the bloodstream (Buonocore et al. (1985) 2 *Proc. Soc. Mag. Res. Med.* 838). (Particles larger than 3 to 5 micron are selectively localized in the lungs, due to embolic entrapment in lung capillaries.) A recent report indicates that the small-sized Gd-liposomes produce effective decreases in liver T1's (as determined spectroscopically without imaging): see Buonocore et al. (1985) 2 *Proc. Soc. Mag. Res. Med.* 838). Also, insoluble Gd-DTPA colloids have recently been reported to enhance MR images of rabbit livers under in vivo conditions (Wolf et al. (1984) 4 *Radiographics* 66 (which is hereby incorporated by reference)). However, three major problems appear to limit the diagnostic utility of these devices. The multilamellar, lipid envelopes of liposomes appear to impede the free diffusion of water protons into the central, hydrophobic cores of these carriers, as assessed by the higher doses of Gd required for in vitro relaxivities equivalent to Gd-DTPA dimeglumine (Buonocore et al. (1985) 2 *Proc. Soc. Mag. Res. Med.* 838). This increases the relative toxicity of each Gd atom.

Even more importantly, these same lipid components cause the carriers to interact with cell membranes of the target organs in a way which leads to a marked prolongation of tissue retention, with clearance times of up to several months. (See Graybill et al., 145 *J. Infect. Dis.* 748 (1982)(which is hereby incorporated by reference), and Taylor et al., 125 *Am. Rev. Reso. Dis.* 610 (1982)(which is hereby incorporated by reference).) Two adverse consequences result. First, image enhancement does not return to baseline in a timely fashion. This precludes re-imaging at the short intervals (ca. 1 to 3-weeks) needed to assess acute disease progression and treatment effects. Second, significant quantities of the liposomally entrapped Gd-DTPA may be transferred directly into the membranes of host cells. (See Blank et al. 39 *Health Physics* 913 (1980)(which is hereby incorporated by reference); Chan et al., 2 *Proc. Soc. Mag. Res. Med.* 846 (1985)(which is hereby incorporated by reference).) This can markedly increase the cellular retention and toxicity of such liposomal agents.

The consequences for Gd toxicity have not yet been reported. Protein (albumin) microspheres with entrapped Gd and Gd chelates have been prepared, and have been determined (by the present inventor and others: see Saini et al. (1985) 2 *Proc. Soc. Mag. Res. Med.* 896) to have only modest effects on T1 relaxivity in vitro. This is because most of the Gd as well as other entrapment materials are initially sequestered in the interior of these spheres, and are released very slowly as the spheres become hydrated (with $t_{\frac{1}{2}}$s of hours). (See Widder et al., 40 *Cancer Res.* 3512 (1980)(which is hereby incorporated by reference).) This phenomenon has been found by the present inventor to markedly reduce the acute (30-to-90-minute) relaxivity of each Gd atom to approximately 1/10th that of Gd-DTPA dimeglumine. Hence, both the quantity of carrier material and the toxicity of Gd are both unnecessarily high.

Emulsions of insoluble, gadolinium oxide particles have been injected into experimental animals, with significant image-enhancing effects on the liver. (Burnett et al. (1985) 3 *Magnetic Res. Imaging* 65). However, these particles are considerably more toxic than any of the preceding materials, and are inappropriate for human use.

Novel Compositions and Methods for Imaging

Because of the significant disadvantages of existing MR image contrast agents, the present inventor has formulated improved agents with reduced toxicity, increased selectivity of tumor and organ uptake, as well as a significant potential for enhancing blood flow images.

A very important consideration, as taught by the present application, is that the marker substance should preferably be selectively deposited at the tissue location which is sought to be imaged. Moreover, the present application also contains significant teachings, regarding how the paramagnetic marker substance is bound to the polymer, which are believed to provide substantial advantages over previous teachings. The present application provides a novel method for NMR imaging, wherein image contrast is very strongly enhanced by a selective transport method which introduces an intramolecularly superparamagnetic strong T1 agent selectively into the desired imaging locations, and specifically into tumor locations. The present application also provides novel compositions of matter which are useful in implementing these methods.

MRI contrast enhancement can be improved moderately in the brain (and greatly in the body, which lacks the brain's tight blood-tissue barrier), by increasing the tumor selectivity of agent uptake.

Injected gadolinium exchanges off of its DTPA chelator at a slow but significant rate in vivo. The resulting free gadolinium forms insoluble oxides, clears slowly from the body, and may produce significant side effects. The present application permits major advantages to be gained, by substituting a less toxic, efficiently cleared, polyatomic metal-atom complex in an improved delivery process.

Chromium, in the form of $^{51}CrO_4^{-2}$, has been used extensively as a clinical agent for radionuclide labeling of platelets and red blood cells. Hexavalent chromate is converted within the red cell to the $Cr^{+3}$ cation, which binds tightly but not irreversibly to hemoglobin. $^{51}$Chromium elutes from red cells at an average rate of 0.93% per day. It is not reutilized by the body, but is cleared efficiently by excretory pathways. It is also of low toxicity in humans, even at relatively large doses. According to studies, in which neutrophils, tumor-cells and other biological targets have been labeled in vitro, $^{51}CrO_4$ has been shown to bind to several cytoskeletal and cytoplasmic proteins (actomyosin as well as hemoglobin), and also to adenine nucleotides. It has also been shown to be nontoxic in vitro at relatively high concentration, as assessed by sensitive measures of cellular metabolism, DNA synthesis and cell division.

When tested as a potential MRI contrast agent, chromium ($+3$) has only moderate potency compared to gadolinium ($+3$), which has the highest number of unpaired electrons (7) of any metal ion. On this basis, the low-molecular-weight gadolinium chelate, Gd-DTPA, was developed as the first clinical MRI contrast agent, even though its small retained fraction (usually less than 0.5%) is substantially more toxic than equivalent quantities of retained chromium, and chromium is cleared much more completely than is gadolinium.

Superparamagnetic Compounds

One class of highly paramagnetic compounds is those in which each molecule includes multiple atoms of magnetic moment with parallel spin vectors. While such intramolecular paramagnetic coupling does not imply that macroscopic ferromagnetic behavior will necessarily occur, it does imply that the resulting compound will be very strongly paramagnetic. Thus, such compounds are referred to as "intramolecularly superparamagnetic."

An article by Bino et al., "$[Cr_4S(O_2CCH_3)_8(H_2O)_4]$: Ferromagnetically Coupled $Cr_4S$ Cluster with Spin 6 Ground State", in the Sept. 16, 1988 issue of Science at page 1479, reported that the paramagnetic potency of chromium can be increased markedly by reformulating it as an intramolecularly ferromagnetically coupled cluster of four coordinated chromium ions, $[Cr_4S(O_2CCH_3)_8(H_2O)_4]^{2+}$. This new, divalent chromium-organic complex cation has 12 unpaired electrons (1.7 times as many as gadolinium), and a magnetic spin of $S=6$ (ground state). The effective magnetic moment of each $Cr^{+3}$ atom in the molecule is increased, due to stabilization of a coordination state which minimizes intramolecular antiferromagnetism.

The Bino et al. article refers to using the disclosed cation as a "spin label". (Spin labeling studies are normally in vitro studies.) The Bino et al. article also notes that the water ligands on the cation are potentially labile, so that the hydration sites would provide ligand bonding sites for association with potential carrier substances.

This tetra-chromium-sulfur-acetate complex is very advantageous for use in formulating MRI contrast agents of high potency and low toxicity. However, its small molecular size would cause it to equilibrate freely with the total extravascular (plasma+extracellular) water (as does Gd-DTPA), thereby reducing its potency and tumor/lesional-site selectivity.

Transport Properties of Polymeric Carrier

The present application teaches that major advantages can be gained by complexing or conjugating a superparamagnetic complex, such as $[Cr_4S(O_2CCH_3)_8(H_2O)_4]^{2+}$, to polymeric or microspheric carriers which restrict its biodistribution, increase its selectivity of tumor localization, and amplify its proton relaxivity by slowing its rotational correlation time.

The present inventor has disclosed, in earlier filings, a method for increasing both the chemical potency (proton relaxivity) and tumor selectivity of paramagnetic contrast agents (including Gd-DTPA), by conjugating them to water-soluble, bio-compatible carbohydrate polymers (including dextrans), whose molecular size distribution ranges from just above the cutoff for filtration out of normal microvessels (ca. 15,000 Daltons) to just below the cutoff for rapid renal clearance (ca. 45,000 Daltons). The present application discloses specific, improved, novel carriers and carrier-polyatomic cluster compositions which give improved site-selectivity even below the formerly taught 15,000 dalton cutoff.

Optimal Size Range

Selectivity of tumor uptake can be conferred in part by the polymeric size, in conjunction with characteristic changes in microvascular surface properties and an increase in porosity of malignant tumor microvessels. This allows the polymeric species (between 15,000 and 45,000 Daltons) to filter or become transported more efficiently out of microvessels into the extra-vascular compartment (tumor interstitium). Due to the low porosity of normal microvessels, polymeric contrast agents are not allowed to filter into the surrounding normal tissues. This property of selective partitioning by molecular size: 1) advantageously results in steeper contrast gradients and increased intensity differences between tumor and normal tissues, and 2) advantageously produces highly discrete identification of tumor margins. However, there are major potential disadvantages to agents greater than 15,000 Daltons in size, as outlined above. Smaller agents, which are still site selective, represent a significant improvement.

Endothelial Binding

Tumor localization is also facilitated by the endothelial binding properties of negatively charged carbohydrates, especially highly sulfated, generally lower molecular weight heparins which are complementary to endothelial/epithelial determinants, including, but not limited to Fraction A heparins of about 6,000 to 10,000 MW. (Simple polysaccharides will normally not adhere to the endothelial wall, unless the polysaccharide includes a charged surface group, such as sulfate, carboxyl, or dicarboxyl.)

Such endothelial binding is reversible and the release of such bound materials occurs much more slowly from tumor microvascular endothelium than from the endothelium of normal tissues. Such prolonged binding at pathologic foci results in selectively accentuated uptake into the tumor interstitial gel proximal to sites of vascular endothelial binding.

Transendothelial Migration

Active endothelial transport has been demonstrated for small molecules (e.q., glucose and insulin). However, no studies other those that of the present applicant are known to have shown such transport for larger molecules, or for molecules carried in a cargo format. It is now known (from the present applicant's histologic studies) that transendothelial migration of particles and molecular aggregates (larger than ca. 2 nm in diameter) can be accelerated by the application of appropriate surface coatings, preferably glycosaminoglycans or anionic polyglucoses or polyglycerols. (The glycosaminoglycans preferably include heparin, heparin derivatives and heparin fragments, but may also include dermatan sulfate, chondroitin sulfate, and other nature or modified glycosaminoglycans, including semisynthetic carboxylated glycosaminoglycans.) These surface coatings will bind multiply to receptors or antigens, which are either synthesized by endothelium or, although synthesized at other sites, become tightly associated with the endothelial surface. (See Ranney, 35 Biochem. Pharmacology 1063 (1986), which is hereby incorporated by reference). Such multiple binding typically involves complementary molecular interactions at more than 5 binding sites per molecule, and preferably more than 10 sites per molecule, and is termed adhesion, surface adhesion, or bioadhesion.

Following extravasation, the new agents in the present application are retained for prolonged intervals in the tumor interstitium (greater than 2.5 hours, as compared to about 10–45 minutes for Gd-DTPA), and remain ("stay put") preferentially in the viable (versus necrotic) subregions. These two properties: 1) allow the agent to be injected at earlier times before imaging (and hence allowing premedication outside the imaging room); 2) permit tumor-treatment effects to be monitored in responding tumor subregions at early post-treatment intervals (at about 6–30 hours); and 3) allow viable and nonviable tumor to be distinguished at submillimeter resolution. This is because dead subregions cease to perfuse (and hence cease to take in the image-enhancing agents), while viable subregions continue to reperfuse and take up image-enhancing agent. Partially damaged subregions continue to perfuse, and, since their microvessels typically have a still-further increased porosity (due to treatment-induced primary or secondary vascular damage), they allow the larger species of polydisperse polymer (as well as the smaller ones) to extravasate into the tumor gel. Hence, the partially damaged and potentially recoverable subregions achieve the brightest image intensity, because they accumulate the greatest quantity of these new, selective contrast-enhancing agents.

A further teaching of the present application is that these anionic glycosaminoglycans, polyglucoses and polyglycerols (and analogous compounds) undergo accentuated uptake by tumor cells, compared to the rate of uptake by normal cells in the same tissue region. This is based on the anionic (negatively charged) nature of side groups present on the polyglucose carriers, which engage the cellular uptake receptors of the anionic transport channels (pores) which are typically induced in hepatocellular carcinomas (hepatomas). Such anionic transport channels have also been found in several other tumor types tested to date (by the present applicant and others). These same transport channels are relatively uninduced in the normal cell counterparts. This property of anionic small molecules and macromolecules facilitates active tumor-cell accumulation of the carrier polymer (and its bound ligands) in vivo. This property is exploited, in the innovative method disclosed herein, to allow for prolonged tumor retention and imaging.

It has previously been shown, by the present inventor as disclosed in a previous filing (International Application PCT/US88/01096), that IMFERONTM $_{TM}$ (which is a tightly bound, iron oxide-dextran complex of about 110,000 Daltons) achieves increased intramolecular paramagnetism (becomes superparamagnetic) overall (e.g., intermolecularly as well). This complex is injected into patients for the purpose of achieving controlled iron release, over intervals of days to weeks, in order to treat iron deficiency anemia. Although it has been injected intravenously into patients, this must be done by controlled rather than bolus infusion, due to the release of a small fraction of its ionic iron which has been associated with acute toxicities. Hence, IMFERONTM TM is usually administered intramuscularly. These problems, together with the requirements, in MR image enhancement, of rapid intravenous administration of relatively large doses of the contrast agent, have precluded the effective use of IMFERONTM TM as an intravascular superparamagnetic contrast agent. However, this experimental evidence provides further confirmation that, as described below, metal coordinates of high potency and lower toxicity can be reformulated as polymeric agents (with a conjugation chemistry which is somewhat analogous to that of IMFERONTM TM). Such metal-coordinate-polymer agents can be administered for purposes of tumor-selective MR image enhancement, or alternatively to provide localized hysteresis superheating.

Use of Microaggregate or Microparticulate Carrier

In one class of embodiments, the carrier is used in the form of nanoparticles and microparticles. As discussed above, these particles have been found (when appropriately surfaced with sites complementary to endothelial determinants) to transport through the more porous parts of the endothelium walls with high preference. This is particularly advantageous in transporting a relatively high dose of the desired substance into the abnormal tissues and cells.

Such a nanosphere is most preferably between about 5 and 99 nanometers, and such a microsphere is most preferably between about 0.2 and 250 micron in diameter. The matrix of the microsphere is preferably a carbohydrate, and may be a carbohydrate such as heparin which also has multivalent binding capabilities especially a Fraction A heparin of about 6,000–10,000 Daltons or fragment thereof larger than about 1,000 Daltons. Protamine, hexadimethrine, starch and other matrix materials can also be used, and can also be coated with heparins. Such a microsphere carbohydrate matrix can optionally include, as a multivalent binding agent, an exposed or covert substance which is capable of binding endothelial surface determinants, enzymes, epiendothelial or subendothelial substances. (Note that the nanoparticle/microparticle matrix may be coated with such a binding substance.)

In such embodiments, the nanoparticles/microparticles of the novel material disclosed herein will bind to endothelia (or to epithelia dn their closely associated extracellular structures), with preference (and longer residence times) in the vicinity of tumors (or other biological lesions if desired). This preferential binding leads to preferential induction, since a bound microsphere may be totally or partially enveloped in, for example, less than 10 to 15 minutes. The interaction of the preferred microspheres with endothelia may produce an induction of the endothelia to undergo transient separation or opening. The opening of the endothelia exposes underlying substances to which (ideally) binding may occur.

The present application provides improved methods and compositions of matter for the selective tumor localization of ferromagnetically coupled image-enhancing agents, contrast agents or spectral shift agents. This permits improved acquisition of tumor, tissue or organ images or spectra from live animals by nuclear magnetic resonance imaging or spectroscopy.

Additional Novel Compositions of Matter

It should be noted that the present application describes not only a number of novel methods, but also a number of novel compositions of matter, as set forth in greater detail below.

One novel teaching of the invention involves use of (I) a ferromagnetically coupled, multiply paramagnetic ion cluster (hereafter also designated the "intramolecularly super-paramagnetic polyatomic complex") which is multiply associated, by complexation (including ion pairing) or covalent conjugation, with (II) a soluble, hydrophilic, biocompatible, excretable polymeric carrier, comprising repeating hydrophilic monomeric units, or with (III) monomeric or oligomeric subunits or fragments of the final polymer, wherein the polymer or polymer subunits (either derived from natural sources or synthetic) have repeating monomeric units with a high frequency of hydroxyl, carbonyl, aldehyde, carboxyl, sulfate, sulfonate, sulfonium, phosphate, phosphonate, phosphonium, amine, amino, or quaternary ammonium groups, singly or in combination on the polymer, and the polymer contains less than about 5% (w/w) cross-linked or microaggregated species, all of low toxicity. The latter groups are for the purposes of either noncovalently binding the superparamagnetic complex or binding to target (including tumor) microvascular endothelium, or binding to both of the preceding entities.

The polymeric agent may optionally be formulated using an excipient counterion to achieve charge balance. Such excipient agents may include, for example, organic amines, preferably including N-methylglucamine (meglumine).

The superparamagnetic complex of the primary preferred embodiments uses a central tetrahedrally coordinated sulfur atom, surrounded by four octahedrally coordinated Chromium atoms, which are stabilized by bridging ligands, (which join pairs of Cr atoms). In the embodiment of Example 10, eight bridging ligands are used, and they are all acetate groups. However, in other embodiments, other bridging ligands, and/or a different number of bridging ligands, may be used.

The polymers most preferably used are Fraction A heparin (or heparan sulfate). However, of course, a large variety of other carrier polymers could be used instead. Note that the preferred polymer molecules are hydrophilic, which is required to provide the necessary environment for reliable NMR results.

Alternative Carrier Compositions

Some of the other polymer species include other dextrans, dextran sulfate, dextran carboxylate, dermatan sulfate, chondroitin sulfate, pentosan polysulfate, hydroxyethyl starch, carboxylated hydroxyethyl starch or CARBETIMER™ TM, carboxylated hydroxyethyl starch, and carboxylated dextrans in which the carboxylating groups consist essentially of multiple closely spaced carboxylates which are thereby capable of undergoing chelation-type or coordination-type binding with polyatomic organometallic complex structures which include metal ions.

The locations of the charged groups in the polymer can be readily modified, by methods well known to those skilled in the art, e.g. by introducing succinylate or glutarylate groups to extend the charge ion groups out from the polymer based structure. Thus, where it is desired to increase the affinity of the polyatomic unit being transported for the polymeric carrier molecule, the conformation of the polymer can optionally be modified in this fashion to achieve a better fit.

Alternative Bridging Ligands in a Superparamagnetic Complex

The bridging ligands in the superparamagnetic complex need not be limited to acetate groups. A wide variety of organocarboxylates may be used. Some examples of alternative bridging ligands include: formate; formaldehyde; glutaraldehyde; glycinate; succinate; acetylacetonate; malonate; propioate; glutarate; hydroxamate; oxalate; 2-bromoacetate; 2-sulfoethanoate, thiolacetate; and thioglycolate.

Use of Reactive Bridging Ligands

The embodiment described below, which includes at least some glycinates as bridging ligands, has the advantage that the glycinates contain sites which can assist in binding. Thus, a further secondary teaching is that the bridging ligand should contain a charged and/or activatable site.

Alternative Paramagnetic Species

The paramagnetic ion which is used in the superparamagnetic complex is most preferably chromium, but may alternatively be one or more of the following species: iron, nickel, manganese, cobalt, vanadium, molybdenum, tungsten, copper, platinum (particularly $^{195}$Pt), erbium, gadolinium, europium, dysprosium and holmium.

Alternative Stabilizing Anions

The superparamagnetic complex $Cr_4S(O_2CCH_3)_8$ is preferably cation is $[Cr_4S(O_2CCH_3)_8(H_2O)_4]^{2+}$. However, other stabilizing species can be used, such as sulfate, halide, nitrate, carboxylate, phosphates, or other stabilizing anions. (Note that some of these anions may be displaced when the complex binds to the endothelia or epithelia.)

Additional Novel Methods

The present application also sets forth a generally applicable method for selective transport of a desired small polyatomic structure into tumors, or other regions of enhanced vascular porosity. Note that these novel teachings can be applied not only to the method of magnetic resonance imaging described, but also to a tremendous variety of other diagnostic and therapeutic uses.

Further Points of Novelty

Among the novel teachings set forth in the present application is a method for magnetic resonance imaging, comprising the steps of: a) identifying a living vertebrate animal to be imagined; b) introducing into the blood stream of said animal a magnetic agent, comprising native or modified heparin or a fragment thereof, of molecular weight between about 1,000 and 10,000 Daltons, and a relatively small polyatomic structure which is intramolecularly superparamagnetic; c) applying to said animal a strong magnetic field which includes a gradient; d) and applying to at least a portion of said animal an electromagnetic perturbation field at a radio frequency generally corresponding to a resonant frequency of a predetermined species at a magnetic field strength which falls within the range of field strengths applied to said animal by said strong magnetic field, and measuring radio frequency response to define a spatial map of magnetic resonance characteristics within tissues of said animal, and e) analyzing said spatial map to determine the extent of tumors or other regions of enhanced vascular porosity.

Also among the novel teachings set forth in the present application is a method as above, wherein the polymeric molecule has a molecular weight of about 10,000 Daltons or less.

Also among the novel teachings set forth in the present application is a method as above, wherein said small polyatomic complex comprises plural atoms of magnetic moment which are mutually ferromagnetically coupled.

Also among the novel teachings set forth in the present application is a method as above, wherein said small polyatomic structure is a polyatomic complex.

Also among the novel teachings set forth in the present application is a method as above, wherein said small polyatomic complex consists essentially of $[Cr_4S(O_2CCH_3)_8(H_2O)_4]^{2+}$.

Also among the novel teachings set forth in the present application is a method as above, wherein said small polyatomic complex comprises multiple atoms of magnetic moment selected from the group consisting of chromium, copper, nickel, manganese, platinum, erbium, gadolinium, erbium, dysprosium and holmium.

Also among the novel teachings set forth in the present application is a method as above, wherein said carrier is selected from the group consisting of: native or modified heparin, heparan sulfate, starch, protamine and hexadimethrine.

In this context, modified heparin, modified heparan sulfate and modified starch may include one or more of the reaction products of: acid hydrolysis, basic hydrolysis, hydrolytic preparation of lower molecular weight fragments than the native (parent) material or purified fraction purified from parent material as obtained from its common source, enzymatic preparation of such fragments from native material or purified fraction of native material, derivitization with substituent groups which can modify association or binding of the polyatomic complex or of heparin, selected from: formate, formaldehyde, glutaraldehyde, acetate, glycinate, succinate, acetylacetonate, malonate, propionate, glutarate, hydroxamate, oxalate, 2-bromoacetate, 2-sulfoethanoate, thiolacetate, thioglycolate, carboxylate, ethylenediaminetetraacetate, diethylenetriaminepentaacetate, hydroxyethyl groups, carboxyethyl groups; reagents comprising multiple carboxylates, carbodiimide linking reagents, other linking reagents, chemical spacer groups, and other chemical derivitizations, alterations of physical conformation and partial degradations which comprise standard chemical and physical reactions performed on heparins, heparan sulfates, starch, simple and complex carbohydrates, and glycosaminoglycans, as well as the reactions (except for proteolysis) listed in the following paragraph.

In this context, modified protamine and hexadimethrine may include one or more of the reaction products of: combining these substances with one or more of native or modified heparin, heparan sulfate, and starch; crystallization, amorphous crystallization, and minor degradation which may occur upon one or more of partial proteolysis, exposure to organic solvents, exposure to mixtures of organic and aqueous solvents, heat, low pressure homogenization, high pressure homogenization, emulsification, combinations of the preceding reactions and processes, and other standard physical and chemical reactions performed on protamine, basic proteins, hexadimethrine and heparin antagonists.

Also among the novel teachings set forth in the present application is a method as above, wherein said carrier has a molecular weight of about 10,000 Daltons or less.

Also among the novel teachings set forth in the present application is a method as above, wherein said small polyatomic structure comprises multiple metal ions mutually ferromagnetically coupled intramolecularly.

Also among the novel teachings set forth in the present application is a method as above, wherein all said constituents of said polyatomic complex, are reduced in standard measures of in vivo toxicity (relative to the free polyatomic complex) in animals and humans when the polyatomic complex is rendered in weak or strong chemical and weak or strong physical association with carrier (as defined above).

Also among the novel teachings set forth in the present application is a method as above, wherein said carrier comprises native or modified Fraction A heparin or a heparin fragment between about ,000 and 10,000 Daltons, which physically formulated as a microparticle having a diameter in the range of about 0.1 micron to 250 microns inclusive.

Also among the novel teachings set forth in the present application is a method as above, wherein said small polyatomic complex is a cation which comprises multiple metal ions ferromagnetically coupled.

Also among the novel teachings set forth in the present application is a method as above, wherein said small polyatomic complex is a cation which comprises multiple metal ions complexed with multiple organic groups free of intermolecular bonds.

Also among the novel teachings set forth in the present application is a method as above, wherein said small polyatomic complex comprises metal ions, and wherein the toxicity of said metal ions is significantly reduced following association with said carrier.

Also among the novel teachings set forth in the present application is a method as above, wherein said small polyatomic complex is ion-pair bound to the interior of said carrier.

Also among the novel teachings set forth in the present application is a method as above, wherein said small polyatomic complex is covalently bound to the interior of said carrier by bonds which include at least one metal-oxide bond.

Also among the novel teachings set forth in the present application is a method as above, wherein a substantial fraction of said charged groups on the interior of said carrier are selected from the group consisting of: sulfides, amides, sites whose charge is strongly affected by an ether bond, and halides.

Also among the novel teachings set forth in the present application is a method as above, wherein said carrier has a molecular weight which is less than about 10,000 Daltons.

Also among the novel teachings set forth in the present application is a method as above, wherein said polymeric molecule has a mean molecular weight of about 8,000 Daltons.

Also among the novel teachings set forth in the present application is a method as above, wherein said carrier has anionic groups at the surface thereof.

Also among the novel teachings set forth in the present application is a method as above, wherein said perturbation field is applied at a frequency which generally corresponds to a resonance frequency of protons in an aqueous environment.

Also among the novel teachings set forth in the present application is an agent for image enhancement or spectral shift comprising: a strongly paramagnetic or intramolecularly superparamagnetic polyatomic complex having a spin of greater than 3/2, more than about 7 unpaired electrons and labile or reactive ligands which can chemically or physically associate with: a biocompatible, excretable, water-soluble carrier comprising heparin having repeating hydrophilic monomeric units having hydroxyl, carboxylate, sulfate, or amine groups, singly or in combination on said carrier: wherein said image enhancing agent has a molecular weight of less than about 10,000 Daltons and is substantially completely water-soluble and contains less than about 5% (w/w) cross-linked or microaggregated species, all of low toxicity.

Also among the novel teachings set forth in the present application is an agent as above, comprising intramolecularly ferromagnetically coupled metal atoms of magnetic moment in association with the carrier, and wherein the image-enhancing agent is used to enhance internal images or shift internal spectra arising from induced magnetic resonance signals.

Also among the novel teachings set forth in the present application is an agent as above, wherein said carrier has a molecular weight between about 1,000 and 10,000 Daltons.

Also among the novel teachings set forth in the present application is an agent as above, wherein said intramolecularly ferromagnetically coupled polyatomic complexes are bound to said carrier noncovalently by a strong ionic (paired-ion or charge) interaction.

Also among the novel teachings set forth in the present application is an agent as above, wherein said carrier has a molecular weight between 1,000 and 10,000 Daltons, and said intramolecularly ferromagnetically coupled polyatomic complex is bound to said carrier by carboxylate or sulfate groups or both which are covalently conjugated to said polymer.

Also among the novel teachings set forth in the present application is an agent as above, wherein said atoms of magnetic moment are selected from said group consisting of chromium, copper, nickel, manganese, erbium, platinum, gadolinium, erbium, dysprosium and holmium.

Also among the novel teachings set forth in the present application is an agent as above, wherein said intramolecularly ferromagnetically coupled polyatomic complex is in a weight proportion to carrier of at least about 1:20.

Also among the novel teachings set forth in the present application is an agent as above, wherein said carrier is selected from the group consisting of: heparin, heparan sulfate, starch, hydroxyethylstarch, carboxylated starch, carboxylated hydroxyethylstarch or carboxyethylstarch.

Also among the novel teachings set forth in the present application is an agent as above, wherein said polyatomic complex consists essentially of $[Cr_4S(O_2CCH_3)_8(H_2O)_4]^{2+}$, Also among the novel teachings set forth in the present application is an agent as above, wherein said polyatomic complex is $[Cr_4S(O_2CCH_3)_8(H_2O)_4]^{2+}$ and said polymer is heparin.

Also among the novel teachings set forth in the present application is an agent as above, wherein said polyatomic complex is $[Cr_4S(O_2CCH_3)_8(H_2O)_4]^{2+}$ and said polymer is DTPA-heparin.

Also among the novel teachings set forth in the present application is an agent as above, wherein said excess anionic charges of said carrier are balanced in part or totally by a nontoxic organic cation (base).

Also among the novel teachings set forth in the present application is an agent as above, wherein excess anionic charge of said carrier is balanced by N-methylglucamine (meglumine).

Also among the novel teachings set forth in the present application is an agent as above, wherein said polyatomic complex is covalently conjugated to said polymer totally or in part by a metal oxide linkage.

Also among the novel teachings set forth in the present application are the following:

1. an agent as above, wherein said intramolecularly ferromagnetically coupled atoms of the polyatomic complex comprise Cr(III), and said carrier comprise heparin having a molecular weight between about 6,000 and 10,00 Daltons, and having binding complementarity to determinants of mammalial endothelia and epithelia;

2. an agent as above, wherein said intramolecularly ferromagnetically coupled atoms of the polyatomic complex comprise four Cr(III) atoms bound to a central tetrahedral sulfur atom and are octahedrally coordinated by bridging species, and said carrier comprises heparin having a molecular weight between about 6,000 and 10,000 Daltons, and having binding complementarity to determinants of mammalian endothelia and epithelia;

3. an agent as above, wherein said polyatomic complex comprises $[Cr_4S(O_2CCH_3)_8(H_2O)_4]^{2+}$ and said carrier comprises heparin having a molecular weight between about 6,000 and 10,000 Daltons, and having binding complementarity to determinants of mammalial endothelia and epithelia;

4. an agent as above, wherein said polyatomic complex comprises $[Cr_4S(O_2CCH_3)_8(H_2O)_4]^{2+}$, and said carrier comprises Fraction A heparin having a molecular weight between about 6,000 and 10,000 Daltons and having binding complementarity to determinants of mammalial endothelia and epithelia;

5. an agent as above, wherein said polyatomic complex comprises $[Cr_4S(O_2CCH_3)_8(H_2O)_4]^{2+}$ and said carrier comprises Fraction A of beef-lung heparin having a molecular weight between about 6,000 and 10,000 Daltons, and having binding complementarity to determinants of mammalian endothelia and epithelia;

6. an agent as above, wherein said polyatomic complex comprises $[Cr_4S(O_2CCH_3)_8(H_2O)_4]^{2+}$, and said carrier comprises native or modified Fraction A heparin or fragment thereof, having a molecular weight between about 1,000 and 10,000 Daltons, and having binding complementarity to determinants of mammalial endothelia and epithelia.

7. an agent as above, wherein said polyatomic complex comprises $[Cr_4S(O_2CCH_3)_8(H_2O)_4]^{2+}$, and said carrier comprises heparin having a mean molecular weight of about 6,000 Daltons, and having binding complementarity to determinants of mammalial endothelia and epithelia;

an agent as above, wherein said polyatomic complex is in association with said carrier noncovalently through a strong ionic, paired-ion or charge interaction, said polyatomic complex comprises $[Cr_4S(O_2CCH_3)_8(H_2O)_4]^{2+}$, and said carrier comprises heparin having a molecular weight between about 6,000 and 10,000 Daltons, and having binding complementarity to determinants of mammalial endothelia and epithelia;

9. an agent as above, wherein said polyatomic complex is in association with said carrier noncovalently through a strong ionic, paired-ion or charge interaction, said strong interaction involves chemical coordination or chelation binding of said polyatomic complex to at least one reactive group of said carrier, each reactive group on said carrier having a coordination number or ionic charge number between 2 and 10, and said polyatomic complex comprises $[Cr_4S(O_2CCH_3)_8(H_2O)_4]^{2+}$, and wherein said carrier comprises heparin having a molecular weight between about 6,000 and 10,000 Daltons, and having binding complementarity to determinants of mammalial endothelia and epithelia;

10. an agent as above, wherein said polyatomic complex is in association with said carrier covalently, and wherein said polyatomic complex comprises $[Cr_4S(O_2CCH_3)_8(H_2O)_4]^{2+}$, and said carrier comprises heparin having a molecular weight between about 6,000 and 10,000 Daltons, and having binding complementarity to determinants of mammalial endothelia and epithelia;

11. an agent as above, wherein association of the polyatomic complex with the carrier is stabilized by heating a predried polyatomic complex plus carrier combination to at least about 100 degrees Celsius in one or more of an organic solvent, and an organic solvent comprising a one or more of a detergent or surfactant, a polyol, a biocompatible oil; and wherein said carrier comprises heparin having a molecular weight between about 6,000 and 10,000 Daltons, and having binding complementarity to determinants of mammalial endothelia and epithelia;

12. an agent as above, wherein association of the polyatomic complex with the carrier is stabilized by heating a predried polyatomic complex plus carrier combination to at least about 100 degrees Celsius in an organic solvent comprising one or more of: acetone, acetone with polyoxyethylene sorbitan mono-oleate between about 0.01 and about 25 weight percent, polyethylene qlycol, glycerol, soybean oil, and corn oil;

13. an agent as above, wherein said polyatomic complex is $[Cr_4S(O_2CCH_3)_8(H_2O)_4]^{2+}$, and wherein association of the polyatomic complex with the carrier is stabilized by heating a pre-dried polyatomic complex plus carrier combination to at least about 100 degrees Celsius in an organic solvent, and wherein pre-drying of the polyatomic complex and use of an organic solvent during heating are to protect said $[Cr_4S(O_2CCH_3)_8(H_2O)_4]^{2+}$ against chemical degradation which can occur slowly for free (carrier-unassociated) $[Cr_4S(O_2CCH_3)_8(H_2O)_4]^{2+}$ in aqueous solvents and which can be accelerated at temperatures substantially above 22 degrees Celsius, and most particularly at temperatures above about 60 to 80 degrees Celsius.

14. an agent as above, wherein said polyatomic complex comprises $[Cr_4S(O_2CCH_3)_8(H_2O)_4]^{2+}$, and said carrier comprises heparin having a molecular weight between about 6,000 and 120,000 Daltons, and having binding complementarity to determinants of mammalial endothelia and epithelia, and wherein the heparin is in combination with one: protamine and hexadimethrine in a reciprocal weight ratio of between about 98:2 and about 2:98;

15. an agent as above, wherein said intramolecularly ferromagnetically coupled polyatomic complex comprises $[Cr_4S(O_2CCH_3)_8(H_2O)_4]^{2+}$, and said carrier comprises Fraction A of beef-lung heparin having a molecular weight between about 6,000 and 10,000 Daltons, having binding complementarity to determinants of mammalial endothelia and epithelia, and wherein the heparin is in combination with one of: starch, hydroxyethylstarch, carboxylated starch, hydroxyethylstarch, carboxyethylstarch, ethylenediaminetetraacetate starch, diethylenetriaminepentaacetate starch, and other modified starch, in a reciprocal weight ratio of between about 98:2 and about 2:98;

16. an agent as above, wherein said polyatomic complex comprises $[Cr_4S(O_2CCH_3)_8(H_2O)_4]^{2+}$, and said carrier comprises Fraction A of beef-lung heparin having a molecular weight between about 6,000 and 10,000 Daltons, having binding complementarity to determinants of mammalial endothelia and epithelia, and wherein the heparin is in combination with one of: dextran, ethylenediaminetetraacetate starch, diethylenetriaminepentaacetate dextran, carboxylated dextran, dextran sulfate, and other modified dextran, in a reciprocal weight ratio of between about 98:2 and about 2:98;

17. an agent as above, wherein said polyatomic complex comprises $[Cr_4S(O_2CCH_3)_8(H_2O)_4]^{2+}$, and said carrier comprises heparin having a molecular weight between about 1,000 and 10,000 Daltons, and having binding complementarity to determinants of mammalial endothelia and epithelia;

18. an agent as above, wherein said intramolecularly ferromagnetically coupled polyatomic complex comprises $[Cr_4S(O_2CCH_3)_8(H_2O)_4]^{2+}$, and said carrier comprises one of: ethylenediaminetetraacetate heparin and diethylenetriaminepentaacetate heparin, the carrier having a molecular weight between about 1,000 and 120,000 Daltons, and having binding complementarity to determinants of mammalial endothelia and epithelia;

19. an agent as above, wherein said carrier comprises heparin between about 1,000 and 10,000 Daltons and is in association with said polyatomic complex, and wherein said polyatomic complex and said carrier are further formulated to compose nanoparticles stabilized by one or more of: chemical binding of two or more carrier substances, heat, homogenization, physical dispersion, and chemical treatment, and wherein the nanoparticle has a mean diameter of between about 5 and 99 nanometers;

20. an agent as above, wherein said carrier comprises Fraction A of beef-lung heparin between about 6,000 and 10,000 Daltons and is in association with said polyatomic complex, and wherein said polyatomic complex and said carrier are further formulated to compose microparticles, which are stabilized by one or more of: chemical binding of two or more carrier substances, heat, homogenization, physical dispersion, and chemical treatment, and wherein the nanoparticle has a mean diameter of between about 0.1 and 250 micrometers;

21. an agent as above, wherein said carrier comprises Fraction A of beef-lung heparin between about 6,000 and 10,000 Daltons and is in association with said associated polyatomic complex, and wherein said polyatomic complex and said carrier are further formulated by combination with at least one of protamine, hexadimethrine, starch, and dextran comprised in said carrier, to compose microparticles, which are stabilized by one or more of: chemical binding of two or more carrier substances, heat, homogenization, physical dispersion, and chemical treatment, and wherein the nanoparticle has a mean diameter of between about 0.1 and 250 micrometers;

22. an agent as above, wherein the proportion of said polyatomic complex to said carrier is at least about 1:20 by weight, in order that sufficient agent can be injected for MRI image enhancement (or spectral shift) without overloading the recipient animal with carrier material;

23. an agent as above, wherein the associated agent plus carrier, prior to any reformulation as nanoparticles or microparticles, contains less than about 5 weight percent cross-linked or microaggregated species, in order to optimize pharmacokinetics (plasma circulation time), biodistribution and body clearance.

BRIEF DESCRIPTION OF THE DRAWINGS

The present invention will be described with reference to the accompanying drawings, which show important sample embodiments of the invention and which are incorporated in the specification hereof by reference, wherein:

FIG. 5A shows an infrared spectrum trace for the reaction products where $Cr_4S(O_2CCH_3)_8$ was heated with glycine in water at 92° C. FIG. 5B shows a trace for the reaction products where $Cr(NO_3)_3$ was heated with glycine in water at 92° C. FIG. 5C shows a trace for the reaction products where $Cr_4S(Ac)_8$ was refluxed in acetic anhydride for severals. FIG. 5D shows a trace for $Cr_4S(Ac)_8$ alone (which has a blue or green color), and FIG. 5E shows a trace for glycine alone.

DESCRIPTION OF THE PREFERRED EMBODIMENTS

The numerous innovative teachings of the present application will be described with particular reference to the presently preferred embodiment, wherein these innovative teachings ar advantageously applied to the particular problems of MRI imaging by selective localization of superparamagnetic molecules. However, it should be understood that this embodiment is only one example of the many advantageous uses of the innovative teachings herein. For example, the various types of innovative methods and compositions disclosed herein can optionally be used to selectively localize radionuclide, x-ray contrast and ultrasound/acoustic image enhancers, or therapeutic agents. In general, statements made in the specification of the present application do not necessarily delimit any of the various claimed inventions. Moreover, some statements may apply to some inventive features but not to others.

Figure 2:
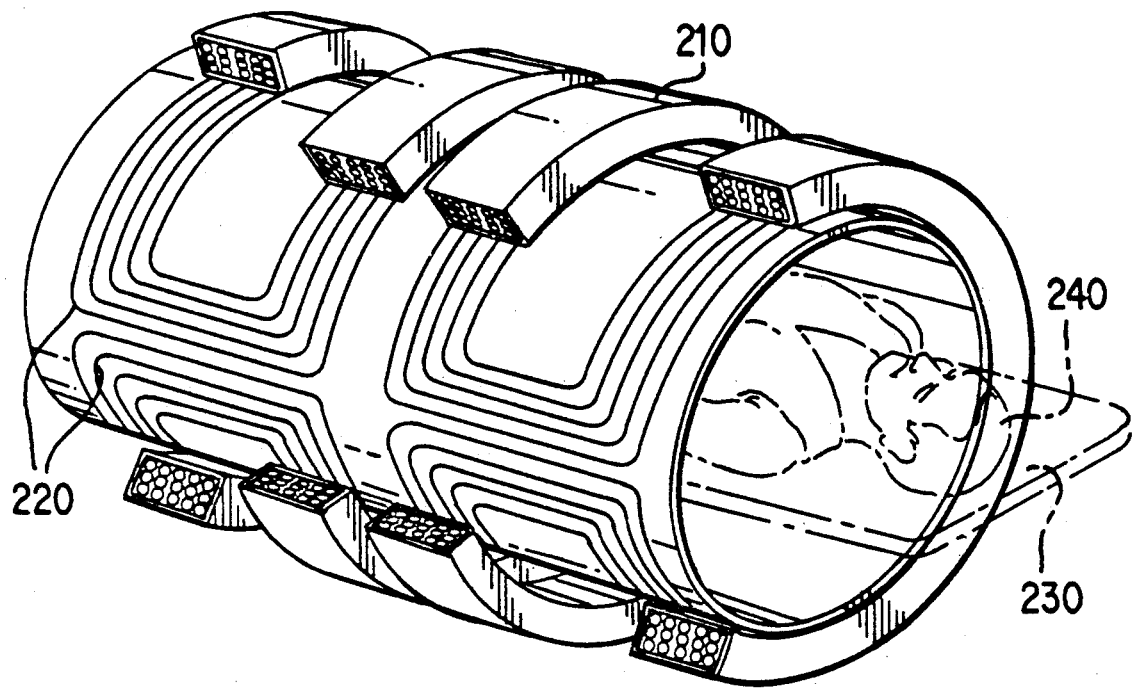
FIG. 2 schematically show a nuclear magnetic resonance imaging system suitable for use in the disclosed innovative method.

FIG. 2 shows an example of a nuclear magnetic resonance imaging (MRI) unit, useable for whole-body imaging of human patients A patient 240 is inserted, on a sliding table 230, into the interior of a large solenoidal winding 210. The large coils 210 (which may be water-cooled or superconducting) will apply a constant (DC) magnetic field, typically 0.5 to 1 Tesla. (This field component is referred to as the $B_0$ field.) Bias coils 220 apply a gradient to this field, as described above. Finally, a probe coil (which is movable, and is not shown in this Figure) is used to apply the RF pulses described above. Differently shaped probe coils are used for imaging different parts of the body, and the probe coil is often shaped so that it will nearly fit to the shape of the surface of the area to be imaged.

The present invention provides an improved MRI imaging method, whereby the ability of MRI systems to detect tumors is greatly enhanced. This is accomplished by selectively introducing an image-enhancing, spectral shift responsive agent into the abnormal tissue.

One novel teaching of the invention involves use of (I) a polyatomic complex comprising plural atoms having magnetic moments which are mutually magnetically coupled within the polyatomic complex, said complex including bridging molecular or atomic species which are individually bound to at least one of said plural atoms having magnetic moments and other atoms of the polyatomic complex, said bridging molecular species being free of intermolecular bonds, more preferably wherein said plural atoms having magnetic moments comprise chromium (III) atoms, more preferably wherein the polyatomic complex comprises four chromium (III) atoms bound to a central tetrahedral sulfur atom and the chromium (III) atoms are octahedrally coordinated by bridging species, and most preferably wherein said polyatomic complex comprises $[Cr_4S(O_2CCH_3)_8(H_2O)_4]^{2+}$; wherein multiple ones of polyatomic complex are associated by one or more of physical means, chemically by noncovalent binding, hydrogen bonding, complexation, strong ionic binding (charge interaction or paired-ion binding), coordination, or covalent conjugation; with (II) a soluble, hydrophilic, biocompatible, excretable, polymeric or oligomeric carrier, preferably comprising heparin in the molecular weight range of about 1,000 to about 10,000 Daltons, and more preferably, rapidly chromatographing Fraction A heparin in the molecular weight range of about 6,000 to about 10,000 Daltons, and most preferably Fraction A heparin in the molecular weight range of about 6,000 to about 10,000 Daltons having a mean molecular weight of about 8.000 Daltons and derived from beef lung; with (III) a fragment or oligomer prepared from (II, above); with (IV) a nanoparticle physical formulation prepared at least in part from (II or III, above), wherein the nanoparticle size is between about 5 and 99 nanometers in mean diameter; with (V) a microparticle physical formulation, prepared at least in part from (II, above) and preferably between about 0.1 and 250 micrometers mean diameter, and most preferably between about 0. and 15 micrometers in mean diameter, wherein said heparin is more preferably rapidly chromatographing Fraction A heparin in the molecular weight range of about 6,000 to about 10,000 daltons, and is most preferably beef-lung Fraction A heparin in the molecular weight range of about 6,000 to about 10,000 Daltons having a mean molecular weight of about 8.000 Daltons; wherein the polymeric carrier (II or III, above) is derived from natural, synthetic or recombinant genetic sources and has repeating monomeric units with a high frequency (by natural or synthetic means) of hydroxyl, carboxyl, aldehyde, sulfate, sulfonate, sulfonium, phosphate, phosphonate, phosphonium, amine, amino, secondary ammonium or quaternary ammonium groups, singly or in combination on the carrier, said groups being for one or more of: association of said polyatomic complex (I, above) with said carrier substances (II or III, above) and binding said polyatomic complex-carrier agent to microvascular endothelium (or epithelium) including the endothelium of tumors and other lesional sites (sites of disease); wherein the weight ratio of said polyatomic complex (I, above) to said carrier (II or III, above) is at least about 1:20; wherein said carrier (II or III, above) is of low mammalian toxicity and contains less than about 5 weight percent cross-linked or microaggregated species; and wherein the carrier may comprise (VI) one or more additional substances in order to provide optimal stability, optimal availability of said atoms of magnetic moment, optimal in vivo properties, (VI) being one or more of native or modified starch, and native or modified dextran, protamine and hexadimethrine, at a weight ratio to heparin of between about 98:2 and 2:98; and (IV) being most preferably protamine. Said atoms of magnetic moment comprise one or more of: chromium, copper, manganese, iron, platinum (particularly 195Pt), cobalt, vanadium, molybdenum, tungsten, gadolinium, erbium, dysprosium, europium and holmium, and preferably comprise chromium (III). Bridging species comprise one or more of: formate, formaldehyde, glutaraldehyde, acetate, glycinate, succinate, acetylacetonate malonate, propionate, glutamate, hydroxamate, oxalate, 2-bromoacetate, 2-sulfoethanoate, thiolacetate, and thioglycolate, and preferably comprise acetate. Additionally, counterions may be used to stabilize the polyatomic complex in various aqueous and nonaqueous solvents and to optimize association with said carrier., Such stabilizing counterions comprise one or more of: halide, sulfate, nitrate, carboxylate and phosphate, and preferably comprise chloride or sulfate. In certain cases and preferably for nanoparticle and microparticle formulations, the association of said polyatomic complex (I, above) and carrier substances (II through VI, above) may be further stabilized by physical means, including (VII) heating a pre-dried polyatomic complex plus carrier substance combination to at least about 100 degrees Celsius in an organic solvent, and in the absence or presence of homogenization, physical dispersion, or emulsification. Said organic solvent preferably comprises one or more of: acetone, a polyol, polyethylene glycol, glycerol, a detergent, a surfactant and a biocompatible oil; more preferably comprises acetone and a biocompatible detergent; and most preferably comprises acetone and polyoxyethylene sorbitan monooleate at between about 0.01 weight percent and about 25 weight percent. Said agent comprising said polyatomic complex (I, above) and one or more carrier substances (II through VI, above) and stabilized according (VII, above), may be further formulated using various excipients or vehicles, including a counterion in order to achieve charge balance. Such counterions may include inorganic or organic amines, preferably including the organic amine, N-methylglucamine (meglumine). The use of such excipients or vehicles may be either for the purposes of in vitro formulation and processing, or for the purposes of improving in vivo properties.

Additional preferred polymer substances include heparin, heparan sulfate, dextrans, dextran sulfate, dextran carboxylate, dermatan sulfate, chondroitin sulfate, pentosan polysulfate, hydroxyethyl starch, carboxylated hydroxyethyl starch or CARBETIMERTM TM, and especially heparin, carboxylated hydroxyethyl starch and carboxylated dextrans in which the carboxylating groups consist essentially of multiple closely spaced carboxylates which are thereby capable of undergoing chelation-type or coordination-type binding with said polyatomic complex structures which include atoms of magnetic moment.

The ferromagnetically coupled polyatomic complex includes a molecular coordination compound containing a paramagnetic metal atom present in numbers of two or more per molecular coordinate, wherein the paramagnetic metal ion includes one or more of the following: chromium, iron, nickel, manganese, cobalt, vanadium, molybdenum, tungsten, copper, platinum (particularly $^{195}$Pt), erbium, gadolinium, europium, dysprosium or holmium; and the complexed metal atoms are stabilized in a ferromagnetic or superparamagnetic intramolecular complex configuration by molecular or atomic bridging species. The preferred metal atoms include chromium and gadolinium, and the preferred bridging species include organosulfates and their derivatives, carboxylic acids, and especially acetate ions. The polyatomic complex may also include a central multivalent stabilizing ion or element, in which case the preferred element includes sulfur. The intramolecularly ferromagnetically coupled, polyatomic complex preferably has a net nuclear spin of greater than about 3/2 and has more than about 7 unpaired electrons. It has one or more of labile water groups a net electrical charge, or reactive groups or combining sites which allow it to chemically associate, covalently or noncovalently with the carrier polymer.

In operation, time-domain windowing may be performed in the MIR imaging run, so that the atoms with the shortest relaxation times are seen preferentially. Alternatively, a high pulse repetition rate may be used, so that the tissues with the longest relaxation times are kept in saturation.

One preferred group of features of the complex for chemical association includes carboxylate, oxygen, metal (especially chromium "hydroxide") glycine amine, and net cationic (positive) charge.

The heparin polyatomic complexes just described, are preferred for selective uptake by systemic tumors, liver and body tumors, lung, lung tumors and other lung lesions, for MRI image enhancement, or hysteresis hyperthermia, following intravenous injection, or particularly for said microparticle formulations, for uptake by solid tumors and other focal disease following selective arterial administration. Lung uptake can be increased by leaving a sufficient fraction of heparin's sulfate groups, preferably greater than 30%, unbalanced by counterions. Lung uptake can be reduced and systemic access increased by balancing more completely the negative sulfate groups of heparin with either or both of the superparamagnetic complex or the excipient counterion, including N-methylglucamine.

In certain instances, it may be preferable to separate the polyatomic complex from the polymeric carrier, using a linker which has a chain length of preferably between about 4 and 8 carbon atoms. This may be desirable under circumstances in which a) the polyatomic complex is a bulky molecule, or b) it is important to stabilize the bond between the polymer and the linker against lysis, including hydrolysis and esterolysis, which may in unusual cases, be catalyzed by a substituent of the polyatomic complex.

In an alternative embodiment, a method of modifying the spatial relation of the magnetic substance to carboxylated carbohydrate polymers, is specified. This alternative method involves derivatizing the carbohydrate polymer with a higher bifunctional acid, including preferably succinic acid, to form a succinylated polymer with a 4-carbon spacer between the polymer and the polyatomic complex to be conjugated to the polymer via the free carboxylate group of each succininate linker.

Although the preceding preferred methods of conjugation have focused on ester and carboxylate linkages, other linkers are not excluded, and in some cases may be preferred. These include aldehyde, amine, amide, carbodiimide, halogen-activated carbohydrate groups, and combinations thereof.

A third preferred embodiment involves providing a physical microsphere or nanosphere form of the preceding agents, in which the diameter of the spheres ranges from 0.1 to 250 micrometers, and the particles are preferably formed from their paired, carrier-polyatomic complexes or from simple mixtures of the polymer and the substance to be entrapped. Matrix polymers and excipients preferably comprise between about 5% and about 75% of the particle weight. The particles are prepared preferably by phase dispersion emulsification (for larger ones) or high-pressure homogenization (for smaller ones), followed by heat or chemical stabilization of the polymer matrix, and extraction of the oil phase with an organic solvent, including acetone, ether, or hexane, preferably acetones which may also contain s small quantity of a biocompatible detergent for surface stabilization, preferably polyoxyethylene sorbitan mono-oleate (or deoxycholate) at about 0.01 to 25% (w/w). Smaller particles are provided by high pressure homogenization. The degree of heat or chemical stabilization will preferably determine how long the particle retains its physical form following rehydration for in vivo administration, and will also determine how rapidly the internally entrapped substance of magnetic moment is made available, hydrated, exposed or released, in order that it can modify the biochemical environment of the plasma, extracellular matrix (or matrix water), or intracellular cytoplasmic substituents (or water). Preferably heat stabilization of carbohydrate matrices is performed for about 30 seconds to 5 minutes, in order to render the matrix sufficiently stabilized that the entrapped material becomes chemically exposed over an interval of about 15 minutes to 30 hours. For both the induction of MRI contrast and the amplification of hysteresis heating, the $t_{\frac{1}{2}}$ for release of entrapped substance of magnetic moment occurs preferably within about 15-20 minutes of injection, although under certain circumstances, particularly those involving the monitoring of controlled-release drugs from selectively localized microcarriers, this $t_{\frac{1}{2}}$ may be considerably longer. Also, for MRI contrast enhancement, the entrapped magnetic material, if paramagnetic, must be hydrated (released) in order to affect surrounding diffusible water protons, whereas, for hysteresis heating, the entrapped material need not be released at all, but can function while still entrapped, providing that the macrodomain size of an average superparamagnetic or ferromagnetic deposit within the particle is sufficiently large for efficient hysteresis to occur, preferably larger than about 0.5 micron. Otherwise, release of entrapped magnetic material with subsequent reconcentration by extracellular matrix binding or cellular processes, is preferred in order to achieve an efficient hysteresis response in the tissues.

The smaller particle sizes (of less than about 10 to 15 micrometers, and especially less than about 3 micron) are preferred for systemic administration by intravenous injection and for selective arterial administration into critical endarterial circulations. The larger particle sizes of greater than 15 micrometers, and especially greater than 100 micrometers are preferred for chemoembolization of selected organs with blood supplies, including especially the liver, by selective arterial administration, and for introduction mechanically, directly into tumor masses or body cavities.

The acute enhancement of blood flow (or perfusion) images, for example in the heart or cerebral vessels, may be accomplished 10 with the soluble polymeric image-enhancing agents and is even more efficiently performed with the nanosphere and microsphere forms.

A significant advantage of MRI enhancement with polymeric, nanoparticle and microparticle formulations, is a further reduction of the dose and any potential toxicity over that which can be achieved by simple (low molecular weight) paramagnetic substances alone.

The relatively rapid biodegradation and metal clearance times, and the resultant shorter reimaging intervals are particular advantages involved with the present invention relative to other polymeric and particulate metal oxides, chelates and complexes.

The image-enhancing agents of the present invention, in soluble nanoparticle or microparticle form, are readily reconstituted for animal and patient administration. This reconstitution involves a simple vortex-type mixing, as contrasted with the sonication in detergents used for protein-based microspheres.

The image-enhancing agents of the present invention are easily usable in any MRI detection system involving administration of paramagnetic, superparamagnetic or ferromagnetic contrast agents. It has particular advantages in conjunction with the newer rapid RF pulse sequences, which reduce native tissue contrast in order to shorten image acquisition times and increase patient throughput. The image or spectral enhancing agents of the present invention allow shorter image acquisition times for satisfactory internal resolutions. These times are generally adequate to produce satisfactory internal images because of the greater enhancement and image contrast produced per unit of superparamagnetic and total agent.

The potential for selective localization of large numbers of relatively nontoxic intramolecularly superparamagnetic molecules by small numbers of monoclonal antibodies, nonpeptide and peptide hormones, lymphokines, cytokines, and other receptor-binding substances tagged with one or more of the innovative (and preferably polymeric) image-enhancing agents is contemplated as a major diagnostic advancement for future use.

The potential for selective localization of large numbers of relatively nontoxic intramolecularly superparamagnetic molecules by small numbers of carrier polymers, nanoparticles or microsparticles is contemplated as a major therapeutic advantage for future use in conjunction with hyperthermia augmentation by hysteresis heating and delivery and monitoring of tagged therapeutic agent localization in sites of disease.

Because of the high MRI contrast conferred by these intramolecularly superparamagnetic substances and the substantial prolongation of lesional residence times, use of the present image-enhancing agents will allow an increased number of serial images to be obtained in an enhancement mode after a single administration of agent.

Due to the selective retention of the carriers used to formulate the present image-enhancing agents, superior definition of tumor margins and markedly improved discrimination of viable and nonviable tumor subregions is possible. This has the major advantage of allowing tumor responses to chemotherapy and radiation therapy to be monitored at early posttreatment times and submillimeter resolution, several weeks before small tumor nodules would regrow to volumes detectible by computerized axial tomography (CAT) and radionuclide scanning.

From a chemical standpoint, some advantages of the present invention may be summarized as follows. When MRI image-enhancing agents comprise intramolecular superparamagnetics, each magnetic substance exhibits an increased (strong) paramagnetic relaxivity for adjacent magnetic nuclei (e.g., protons) and hence, gives greater T1-weighted signal enhancement. This increased relaxivity is related to an increased dipolar correlation time of the superparamagnetic substance due to its slower molecular rotation when polymerically controlled. Spacer groups are not required between the intramolecularly superparamagnetic substance and the polymeric carrier in order to obtain optimal paramagnetic relaxation potencies, however, they could be introduced if deemed advantageous for other purposes.

The chemically defined nature of preferred polyatomic complex-carrier combinations allows ready batch-to-batch uniformity for improved pharmaceutical formulations and a likely greater ease of regulatory approval.

Many of the preferred polymers of the present invention, such as certain dextrans (40,000 and 70,000 MW forms), hydroxyethyl starch, and heparins, for example, have already separately achieved final regulatory approval for patient administration. The size of these polymers is optimized to prevent access into normal tissues, but to still allow rapid renal clearance and essentially complete body clearance. This is especially true for the present novel heparins of less than about 10,000 Daltons. Also, due to the association of multiple, intramolecularly superparamagnetic substances with each polymeric carrier molecule, the resulting complexes and conjugates comprise low osmolality agents by comparison to their low-molecular weight counterparts. Such low osmolality agents have been shown to have major advantages in several categories of high-risk (particularly cardiovascular) patients.

For parenteral administration, these agents are preferably formulated as a sterile, physiologically balanced, aqueous solution (or suspension), whose pH for purposes of intravenous administration is 6.5 to 7.0. Alternatively, these agents may be lyophilized and provided in the dried form for reconstitution in physiologic solutions just prior to administration. For injection into body cavities (such as the bladder, uterus, Fallopian tubes, nasal sinuses or ventriculo-cerebrospinal system), these agent may be formulated as a physiological solution (or suspension) which contains additional substances (excipients) to increase the viscosity or osmolality. Other additives and formulations may also be incorporated according to standard pharmaceutical procedures.

For parenteral administration, the concentration of total active agent (polymer-superparamagnetic substance) will be between about 0.1% and 30% (weight/volume), typically between about 5% and 25%, and preferably about 20%. Doses of the soluble polymer, nanoparticle and microparticle agents will vary depending on the superparamagnetic substance used and the route of administration. The following doses are given for intravenous administration. For tumor image enhancement with some of the preferred embodiments, which include soluble $Cr_4S(O_2CCH_3)_8(H_2O)_4^{+2}$ complexed to heparins, the dose of chromium will be between about 0.005 and 0.01 millimoles per kilogram of body weight. For enhancement of the cardiovascular blood pool, the optimal dose will occur at or below about 0.04 and 0.3 millimoles of chromium per kilogram.

For hysteresis heating, the nanosphere or microsphere forms of agents will be administered once or multiply, at about 15 minutes to 2 hours prior to each treatment by either systemic intravenous injection, direct administration into superficial tumors, or by intraarterial perfusion, at doses of up to 1.0 mmol/kg of the superparamagnetic substance. Hysteresis hyperthermia at a frequency of about 10 to 150 kHz will be directed from an external oscillating magnetic source whose maximal energy displacement is centered over the major external or imageable mass(es) of tumor. A major anticipated advantage of using the nanosphere or microsphere form of preferred embodiment, is that a high concentration of clustered (macrodomain) metal is selectively localized in the diseased subregions of the target tissue following transvascular administration, and this localized material further concentrates in the viable, most heavily perfused subregions of tumor which require the greatest augmentation of heating to compensate for their disproportionate loss of heat due to blood flow dissipation.

Figure 3:
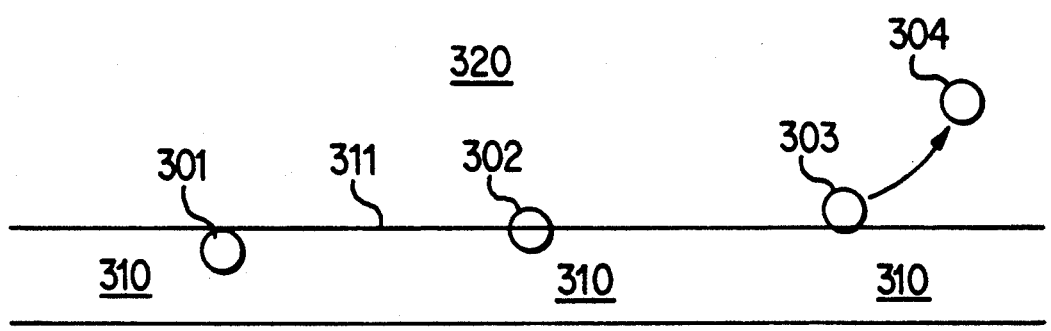
FIG. 3 is a schematic representation of the transport of microspheres entirely across endothelial (or epithelial) tissue.

FIG. 3 schematically shows how the trans-epithelial transport of microspheres works. A small blood vessel 310 is shown passing through tissue 320. Four microspheres (or nanospheres) 301, 302, 303, and 304 are shown at different stages of passage.

Microsphere 301 has recently adhered to the endothelial wall 311. Thus, this microsphere is said to be at the stage of endothelial adhesion.

Microsphere 302 is at the stage of endothelial envelopment. This will occur after a few minutes, as the wall 311 gradually covers a particle (like microsphere 301) which has adhered to it.

Microsphere 303 is shown at the further stage of extravasation, after envelopment has passed it entirely across the endothelial (or epithelial) wall 311.

Finally, microsphere 304 is shown at yet a further stage, of percolation through tissue.

Figure 4:
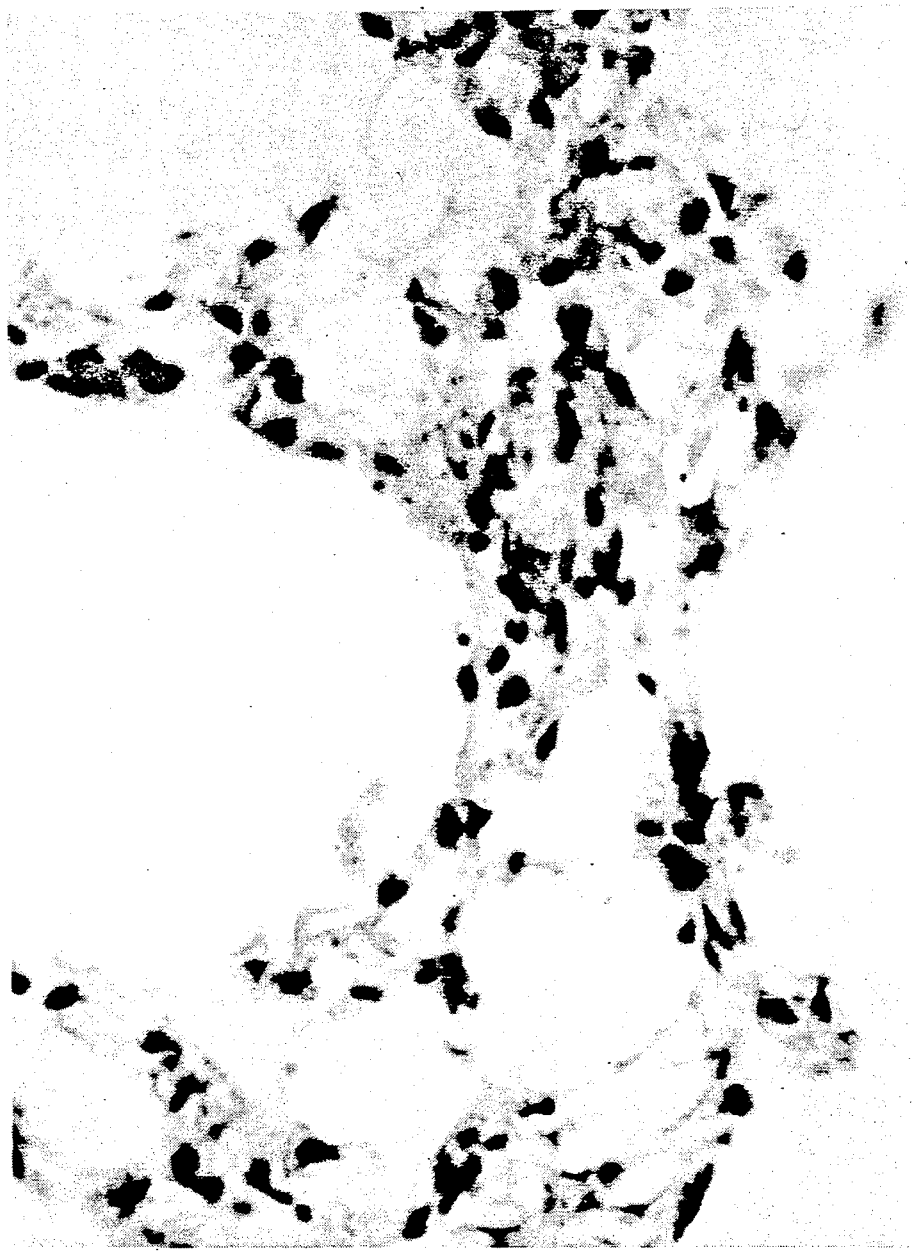
FIG. 4 is a photograph of stained tissue showing localization of nanospheres. The nanospheres, at the scale of this photograph, appear as small gray round or oval dots of 1 to 2 $\mu$m in diameter.

FIG. 4 is a photograph of stained tissue showing lung localization of heparin-coated subembolizing (0.1–0.8 micron) nanospheres distributed throughout rodent lung tissue at 5 minutes after intravenous injection via the tail vein. The nanospheres, at the scale of this photograph, appear as small gray round or oval dots of 1 to 2 mm in diameter.

The following examples are presented to illustrate preferred embodiments of the present invention and their use in MR imaging or hysteresis heating. These examples are purely illustrative, and do not in any way delimit the full scope of the present invention.

EXAMPLE 1

Preparation of DTPA-Dextrans

The cyclic dianhydride of DTPA (diethylenetriamine pentaacetic acid), as prepared by the method of Eckelman et al. (J. Pharm. Sci. V 64, pp 704–706 (1975), was obtained in a highly pure form from Calbiochem-Bhering Corp. The completely soluble DTPA derivative of dextran was prepared by adding 7.0 g of the cyclic DTPA dianhydride stepwise to 1.72 g of Dextran T70 (average MW 70,000 Daltons, MN 46,000, Pharmacia Chemicals) in a reaction solvent comprising HEPES buffer 115 mg/100 co distilled water, pH 7.0 to 8.0. The reaction was carried out with vigorous stirring at ambient temperatures for 1 hr with readjustment to pH 7.0 using NaOH, after the addition of each aliquot of DTPA dianhydride.

The dextran-DTPA product was separated from unconjugated DTPA by dialysis against 200 volumes of 0.15 N NaCl and then 50 volumes of distilled water at pH 6.5. This and the following step are major improvements over the derivatization method previously filed by the present inventor. (See U.S. patent application Ser. Nos. 799,757 and 086,692, and PCT Application PCT/US86/02479, which are hereby incorporated by reference.) Upon completion of dialysis, the conjugate was brought again to 115 mg/100 cc in HEPES buffer, and reacted a second time with an identical quantity of DTPA dianhydride as described above. After this, the dialysis was repeated as described above.

As assessed by molecular filtration, 98% of the dextran-DTPA product had a molecular weight of less than 100,000 Daltons. The dilute solution of DTPA-dextran was either: a) concentrated to between 10% and 25% (w/v) by forced filtered-air evaporation at room temperature, or b) lyophilized to dryness for prolonged shelf storage. Concentrated salts and buffers were added as needed, to render the final preparations physiologically acceptable for injection. The pH was maintained between 6.5 and 7.0. As assayed by complexometric titration, one ligand of DTPA was conjugated for every 7 sugar residues, for a total of 55.5 DTPAs per 389 glucose units in each average molecule.

Two other soluble DTPA-dextran derivatives were synthesized from dextrans of starting molecular weights=10,000 Daltons (Dextran T10, Pharmacia Chemicals) and 40,000 Daltons (Dextran T40, Pharmacia Chemicals). All of the preceding dextrans were soluble and free of microaggregates, as assessed by filtration through serial molecular sieve filters (Amicon Corporation).

EXAMPLE 2

Preparation of DTPA-Hydroxyethyl Starch

Low-molecular-weight hydroxyethyl starch is obtained in a highly pure and soluble form from American Critical Care/DuPont, reacted with the cyclic dianhydride of DTPA, and the polymeric derivative separated, concentrated and titrated as described in EXAMPLE 1.

EXAMPLE 3

Preparation of Succinylated-Dextrans

Succinyl anhydride is obtained in a highly pure form from Aldrich Chemicals, and reacted with dextrans of 40,000 MW and 70,000 MW, and the polymeric derivative separated, concentrated and titrated as described in EXAMPLE 1.

EXAMPLE 4

Preparation of the Paired-Ion Metal Co-Ordinate-Polymer Complex Cisplatin-DTPA-Dextran (70,000 MW)

Lyophilized DTPA-dextran (70,000 MW), prepared as in Example 1, was dissolved in 1.4 cc of sterile water, heated for 30 seconds by swirling in a boiling water bath, added (hot) to 70 mg Platinol TM powder (containing 3.33 mg of cisplatin, $Pt(NH_3)_2$-$Cl_2$ with the remaining weight comprising excipients; Bristol Laboratories), the solution vortexed vigorously for 30 seconds to dissolve the Platinol TM +excipients, and the resulting solution cooled to room temperature and checked for complete solubility at 2.4 mg/ml. Formation of a stable paired-ion complex between the platinum coordinate and the carboxyl groups bound to dextran, was established by three tests: a) continued solubility of cisplatin at a concentration greater than its native solubility limit of 1.5 mg/cc; b) reduction in the complexation of exogenously added calcium ions by the DTPA groups of DTPA-dextran (assessed using an Orion Instruments ionized calcium analyzer); and c) elimination of tetany following intravenous injection of the resulting mixture into CBA/J mice (Jackson Laboratories) at a dose of 10 mg/25 gm body weight. This absence of tetany contrasts with the occurrence of tetany and death in mice which were injected with an equivalent dose of DTPA-dextran alone—and importantly, in the absence of balancing quantities of calcium ion, which render the resulting Ca-DTPA-dextran entirely nontoxic in vivo. Hence, by in vitro and in vivo criteria, cisplatin (as Platinol TM) undergoes complexation to DTPA-dextran at a sufficient binding stability to compete with an added, divalent metal cation ($Ca^{+2}$) The exact coordination state and chemical structure of the resulting cisplatin-DTPA-dextran complex has not been further elucidated.

EXAMPLE 5

Preparation of the Paired-Ion Metal Coordinate-Polymer Complex, Cisplatin-Heparin (22,000-26,000 MW)

Beef-lung heparin (Upjohn Company) 6,000-10,000MW was added dry at 14 mg to 280 mg of dry Platinol TM powder (Bristol Laboratories) containing 14 mg of cisplatin, the mixture dissolved in 14 cc of sterile water and vortexed for 1 minute to completely dissolve all components. Formation of a stable paired-ion complex between the platinum coordinate and the sulfate groups covalently bound to heparin, was established by two tests: a) continued solubility of cisplatin at a higher concentration (2.25 mg/cc) than its native solubility limit of 1.5 mg/cc; and b) alteration of cisplatin biodistribution following intravenous and intraarterial injection in animals (see the Examples below).

Example 6

Preparation of Heat-Stabilized, Hydroxyethyl Starch-Matrix Microparticles Which Encapsulate Cisplatin and Have a Heparin Surface Coating Hydroxyethyl starch 605 mg (Sigma Chemicals) was suspended in 5.5 cc of sterile water and heated for 3 minutes in a boiling water bath to bring it into a stable (translucent) emulsion, and 5 cc of this was added to 1000 mg of Platinol TM (Bristol Laboratories) containing 50 mg of cisplatin. This was emulsified for 30 seconds in 70 cc of heated (100° C) cottonseed oil (Sargent Welch) using a Brinkmann Instruments ultrasonic homogenizer, and the oil cooled in a room-temperature water bath, with continued homogenization for 2 more minutes, until the emulsion itself reached room temperature. This was extracted 4 times with acetone (Fisher Chemicals) containing 0.5% Tween 80 (Sigma Chemicals), and was harvested by centrifugation and air dried. The resulting microparticle diameters ranged from 0.1–1.0 micron.

A heparin coating was applied to the particle surfaces by adding 2 cc of a water solution containing 50 mg of beef-lung heparin (Upjohn Company) 6,000–10,000 MW, adding the particle suspension plus heparin to 70 cc of heated (100° C.) cottonseed oil and repeating the emulsification and extraction steps described in the preceding paragraph. The resulting particles ranged from 0.1 to 0.8 micron in diameter. The presence of a heparin surface coating was verified by suspending the particles in normal saline and adding protamine (Sigma Chemicals), a multivalent heparin-binding agent. This produced aggregation and agglutination of the heparin-coated (but not uncoated) particles.

EXAMPLE 7

In Vivo Testing For Selective Lung Localization of the Preceding Preparations Following Intravenous CBA/J mice (Jackson Laboratories) were injected intravenously via the tail vein with a) small microparticles containing a heparin surface (as in Example 6) and b) soluble heparin-cisplatin complex-es (prepared as in Example 5). At 5 to 15 minutes postinjection, the animals were sacrificed, their lungs removed and fixed with intratracheal buffered formalin, tissue sections cut at 8 microns thickness, and the sections stained using a newly devised method for platinum which comprises a microwave-augmented iron-type stain (60° C. ×2 minute×3 cycles) using a 1:1 mixture of 2% ferriferrocyanide reagent and 4% HCl. By this method, lung uptake of both the small microspheres (see FIG. 4) and soluble paired-ion complex of cisplatin-heparin was documented at the 5-minute postinjection interval. Rapid uptake occurred in both extracellular and intra-cellular compartments, and additional histochemical positivity of bronchial respiratory epithelium and paratracheal lymph nodes was observed at 10–15 minutes. No significant staining was observed following intravenous injection of a standard formulation of Platinol (Bristol Laboratories). To those skilled in the art, additional evidence for selective lung localization, was obtained by injecting intravenously, analogous (subembolizing) heparin-coated small microparticles containing encapsulated amphotericin B, into identical mice, homogenizing the lungs, and documenting an 8-fold increment in drug levels over native amphotericin B (deoxycholate formulation, Fungizone; Squibb) recovered at 1 to 3 hours postinjection. (See U.S. patent application No. 07/033,432, and PCT application PCT/US88/01096, which are hereby incorporated by reference.) Hence, the preceding histologic stains correlated with an increment of nearly 1 order of magnitude in selective pulmonary carrier and drug localization.

EXAMPLE 8

In Vivo Testing For Selective Tumor Localization of the Preceding Preparations Following Intraarterial Administration Additional documentation for maintenance of the cisplatin-carrier paired-ion complex in vivo was obtained as follows. Rabbits bearing VX2 carcinomas of the right hind limb were catheterized under fluoroscopic control, and three of the preceding Platinol formulations, as well as standard Platinol, were injected at a constant dose of 15 mg (of cisplatin) per rabbit by selective arterial perfusion over 15 minutes, into the tumor-bearing limb. Animals were sacrificed at 15 minutes, and the tumors and organs were homogenized extracted and analyzed by atomic absorption for tissue platinum concentrations, as shown in Table 1.

TABLE 1

| Platinum content (ng/mg of tissue, wet weight)-Ipsilateral | | | | | |
|---|---|---|---|---|---|
| Agent | Blood | Tumor | Muscle | Liver | Kidney |
| Heparin-cisplatin: | 2.71 | 12.24 | 0.18 | 5.74 | 5.88 |
| DTPA-dextran cisplatin: | 2.14 | 10.81 | 0.29 | 3.47 | 2.92 |
| Heparin-coated hydroxyethyl starch small microspheres of cisplatin: | 2.43 | 14.07 | 0.20 | 4.64 | 5.91 |
| Standard: | 2.36 | 8.40 | 1.09 | 6.09 | 4.09 |

Additionally, histochemical platinum stains were performed on the tumor tissues, as described in Example 7. These stains revealed intracellular tumor-cell (but not normal-cell) platinum in all of the groups in Table 1 except group 4. Moreover, the intracellular staining of tumor cells in groups 1–3 was significantly more intense than the background staining of hemoglobin iron in red blood cells. Since hemoglobin iron is present at a mean corpuscular hemoglobin concentration (MCHC) of about 0.2 molar, these results suggest strongly that tumor cell platinum reaches very high concentrations relative to those achieved with standard Platinol TM. To individuals skilled in the art, this also indicates that selective tumor-cell augmentation of hysteresis heating may be achieved by first administering one or more of the carrier formulations described above, but in stable complexation with a strong superparamagnetic substance which is otherwise too small and uncontrolled to undergo this degree of selective localization.

EXAMPLE 9

Prolonged Enhancement of Human Tumor (Melanoma) Xenografts in Nude Mice, by Paramagnetic Chelate Associated Covalently with Dextran 70

The strong paramagnetic metal ion, gadolinium ($Gd^{+3}$), was chelated stoichiometrically to DTPA-Dextran 70 polymer, whose preparation is described in Example 1, paragraph 2 (improved formulation). Swiss nude mice were inoculated with BRO-strain human malignant melanomas, and these were allowed to grow to a 1–1.5 cm diameter. Moderately T1-weighted MR imaging (TR=500 msec, TE=40 msec) was performed in a standard Diasonics ™ medical imager and a 30-cm RF head coil, before and after intravenous injection of equivalent doses of Gd-DTPA-Dextran-70 (0.03 mmol Gd/kg) or Gd-DTPA (0.1 mmol/kg) contrast agent. Gd-DTPA-dextran and Gd-DTPA began to optimally enhance the tumors at comparably short postcontrast intervals of 10 minutes, however, by one hour Gd-DTPA had completely faded, whereas Gd-DTPA-dextran continued to enhance these tumors intensely for longer than 2.5 hours (the cutoff time on imaging experiments). To those skilled in the art, it will be recognized from these results that chelated Gd and small metal coordinates in general, will benefit greatly in terms of potency (by at least half an order of magnitude), tumor selectivity and tumor retention, from covalent conjugation or strong paired-ion association with dextran or including analogous carbohydrate carrier molecules. It will also be recognized that much lower doses of the stronger superparamagnetics (including doses below about 0.01 mmol/kg, versus 0.1 mmol/kg for Gd-DTPA) can be used to obtain effective MRI contrast enhancement; and that much faster, more heavily T1-weighted pulse sequences can be implemented in the presence of intramolecularly superparamagnetic polyatomic complex-carrier polymer conjugates or paired-ion complexes.

In the preceding study (see PCT Patent Application PCT/US88/01096), $^{153}$Gd-DTPA-dextran was documented to clear from the blood with a $t_½$ of about 50 minutes (versus 20 minutes for Gd-DTPA). Total body clearance was almost complete (greater than 96%) by 24 hours. Hence, to those skilled in the art, it will be recognized that strong association of a metal coordinate with this polymeric carbohydrate of predominantly less than 50,000 MW, and particularly with a polymeric carbohydrate with substantially lower molecular weight of less than 10,000 Daltons, allows rapid and complete blood and body clearance by predominantly renal pathways.

EXAMPLE 10

Preparation of Paired-Ion Molecular Complexes of $Cr_4S(O_2CCH_3)_8(H_2O)_4^{+2}$ With Negatively Charged Polymeric Carbohydrate Carriers The following negatively charged polymeric carriers are obtained for individual addition and ion pairing to the ferromagnetically coupled polyatomic cation complex $Cr_4S(O_2CCH_3)_8(H_2O)_4^{+2}$ (Exxon Corporation)(see the Bino et al. article cited above): heparin (6,000-10,000 Daltons, Upjohn Company); DTPA-dextrans (40,000 and 70,000 MW parent carbohydrates, derivatized as in Example 1); DTPA-hydroxyethyl starch (50,000 MW parent carbohydrate, prepared as in Example 2); and succinylated-dextrans (40,000 and 60,000 MW parent carbohydrates, derivatized as in Example 3). Each polymer is added as a concentrated aqueous solution, at stoichiometric charge equivalency, or at 50% or 25% of charge equivalency, to a concentrated aqueous solution of $Cr_4S(O_2CCH_3)_8(H_2O)_4^{+2}$ as the chloride salt. Ion pairing is achieved by direct mixing and heating for 1-5 minutes to 100° C. at pH 7, with vigorous stirring. To subfractions of the 25% and 50% mixtures (above) is added a concentrated aqueous solution of N-methylglucamine at quantities sufficient to achieve electrical neutrality. The stability of ion pairing is tested by performing equilibrium dialysis against 200 volumes of 0.15 N NaCl and assaying the retained (polymeric) materials for T1 relaxivity (IBM PC20 NMR Spectral Analyzer). Those skilled in the art will recognize from the results of cisplatin complexation to heparin and DTPA-dextran (documented in Examples 4 and 5) that. the even more positively charged $Cr_4S(O_2CCH_3)_8(H_2O)_4^{+2}$ counterion of the present example results in an even stronger ion pairing to heparin and DTPA-dextran than the satisfactory (in vitro and in vivo) pairing achieved for the cisplatin metalamine coordinate documented in Examples 4 and 5.

EXAMPLE 11

Preparation of $Cr_4S(O_2CCH_3)_8(H_2O)_4^{+2}$ Bound to Heparin

Beef-lung heparin Fraction A (6,000-10,000MW) is obtained (Hepar Corp.) for individual binding to the polyatomic chromium complex, $Cr_4S(O_2CCH_3)_8(H_2O)_4.Cl_2$ (Chiron, Trondheim, Norway). Since the chromium complex is relatively unstable to prolonged heating in water, this reaction is carried out over a short interval in absolute ethanol (USP) (in which the chromium complex shows markedly increased stability to heating) and under increased pressure, using a microwave digestion bomb (Berghof America). The heparin is sonicated into the ethanol as a very fine solid dispersion. The chromium complex is added under concentrated conditions of 250 mg/ml, in order to take advantage of its autoprotection at higher concentrations against degradation in hot solvents. This mixed dispersion/solution is placed in the digestion bomb, the bomb is sealed, the sealed bomb is placed into a preheated, 135C glycerol bath for 5 minutes, the reaction is carried out with very rapid magnetic stirring, and then the bomb is transferred into water at room temperature in order to achieve rapid cooling to ambient temperature. The resulting product remains as a very fine dispersion whose size varies depending on the size of the heparin at input. This size ranges from about 100 nanometers to about 10 micrometers in mean diameter. The resulting products respectively, are centrifuged at 22,000×g for 10 to 15 minutes, and binding of the chromium complex together with retention of at least partial integrity (greater than about 50%) of the chromium complex are verified by UV measurements at the characteristic maxima of 600 nanometers.

EXAMPLE 12

Preparation of $Cr_4S(O_2CCH_3)_8(H_2O)_4]^{+2}$ Bound to Diethylenetriaminepentaacetate Heparin and to Diethylenetriaminepentaacetate Dextran Beef lung heparin Fraction A (6,000-10,000 MW) is obtained (Hepar Corp.) for individual binding to polyatomic chromium complex, $[Cr_4S(O_2CCH_3)_8(H_2O)_4].Cl_2$ (Chiron, Trondheim, Norway), and is dissolved in distilled water at 25 mg/ml. Diethylenetriaminepentaacetate (DTPA) heparin and DTPA dextran are prepared as in Example 1, and are added respectively, to the chromium complex in aqueous solution, such as to give a molar ratio of 0.4 moles of DTPA carrier to 1.0 moles of chromium complex. The respective reactions are carried out by placing the reaction tubes into a beaker of boiling water for preferably 60 to 90 seconds, and then immediately quenching the reaction by transferring these reaction tubes into a beaker of room temperature water. Evidence for transchelation binding of the chromium complex by carrier-bound DTPA comprises: a) molecular filtration retention of the characteristic blue color above a 3,000 Dalton molecular cutoff filter; and b) a downward shift in the UV absorbance maximum of the resulting product from the native 600 nm peak of native chromium complex, to about 560 nm. A slight to moderate decrease in absorbance intensity is observed, suggesting that some degradation of the chromium complex accompanies this reaction. However, such degradation is not to that of comparably heated chromium complex alone, which retains an absorbance maximum of 600 nm. Additionally, such degradation is not to that of chromium complex alone, comparably heated, or of chromium complex plus a two-fold molar excess of DTPA comparably heated, both of which have characteristically distinct UV absorbance maxima and absorbance peak height ratios for their characteristic two absorbance maxima at about 500–600 nm and about 390–450 nm. Hence, there is strong evidence for formation of stabilized polymeric chromium complex-heparin and chromium complex-dextran 70 agents, wherein binding is by partial transchelation of the chromium complex to the DTPA groups of the carriers. Further evidence involves preservation of at least about 60-80% of the native Rl relaxivity of the free chromium complex.

INSERT 6

Figure 1:
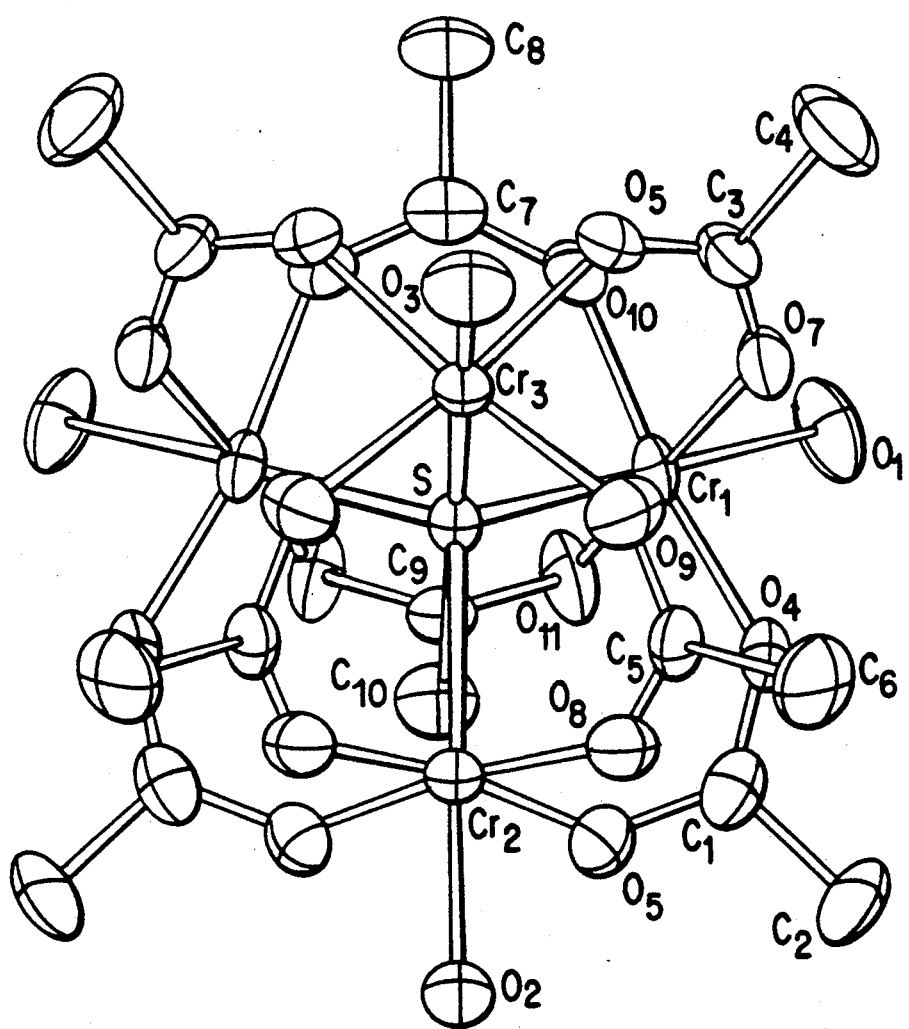
FIG. 1 shows a perspective view of a sample superparamagnetic complex which can be used in one embodiment of the disclosed method.

FIG. 1 shows a perspective view of the $Cr_4S(O_2CCH_3)_8(H_2O)_4^{+2}$ cation (excluding hydrogen atoms). The atoms are shown with ellipsoids, to indicate approximate thermal vibration ranges at room temperature.

EXAMPLE 13

ADVANTAGES TO NMR IMAGING OF POLYMERIC FORMULATIONS OF CARRIER FERROMAGNETICALLY COUPLED POLYATOMIC COMPLEXES

Selected polymeric formulations of $Cr_4S(O_2CCH_3)_8(H_2O)_4^{+2}$, prepared as described in the preceding Examples, are injected intravenously to obtain systemic lesional uptake (frequently practiced in radiology), or intraarterially (less frequently practiced in radiology), to obtain highly selective uptake in regional tumors, especially of the liver, pelvis, brain and limbs. Those skilled in the art will recognize that the more potent, more selective, less toxic (including especially chromium nontoxicity) polymeric formulations of superparamagnetics, including $Cr_4S(O_2CCH_3)_8(H_2O)_4^{+2}$ and analogous cluster compounds incorporating ions such as $Gd^{+3}$ or $Fe^{+3}$, advantageously allow the dose of paramagnetic, including chromium, to be reduced to less than about 0.005 to 0.01 mmol/kg of body weight. (See Ranney, Contrast Agents in Magnetic Resonance Imaging, in Excerpta Medica at page 81 (1986), which is hereby incorporated by reference). It will also be recognized that MRI procedures involving fast imaging (see Bluem et al., 157 Radiology 335 (1985), which is hereby incorporated by reference) and cardiovascular MRI (including MRI "angiography") (see Nagler et al., 157 Radiology 313 (1985), which is hereby incorporated by reference) will benefit greatly, in terms of shortened image acquisition time and improved quality, from a nontoxic contrast polymer of superparamagnetic potency. Additionally, the polymeric polyatomic-complex agents described in the preceding Examples are useful for co-labelling either therapeutic drug carriers (polymeric or nanoparticulate) or the therapeutic agents themselves, whose tumor (or other lesional) localization needs to be monitored and whose rate of release from the carrier (bioavailability) needs to be assessed noninvasively in vivo, potentially in multiple lesions at different depths within a body region. In this context, polymeric polyatomic-complex agents are useful and of improved utility due to increased potency and selectivity, and reduced toxicity. Furthermore, increased potency allows drug release to be monitored over longer postinjection intervals within target tissues, organs, tumors and infections. These improvements are based on the present application, and also, in part, on applicant's earlier-reported work on the use of partially analogous, but less potent, Gd-DTPA-dextran-labelled drug carriers leading to localization in tissues and enhanced MRI detection. (See the Ranney and Huffaker article at 507 Proc. N.Y. Acad. Sci. 104 (1987), which is hereby incorporated by reference.)

EXAMPLE 14

Advantages to Hysteresis Heating of Polymeric Formulations of Ferromagnetically Coupled Polyatomic Complexes Microinhomogeneities of tissue heating represent a major problem in hyperthermia treatment of tumors. This results in considerable part, from the selective survival of tumor cells lying adjacent to microvessels—in which heat loss is accentuated by blood flow. A partially effective approach to this problem has been to inject small ferromagnetic particles of $Fe_2O_3$ directly into the tumor masses, and then apply magnetic hysteresis heating at frequencies of 10–100 kHz to the entire local region. (See Borelli et al., 29 Phys. Med. Biol. 487 (1984). Effective superheating and tumor regression in mice occurs if the injected magnetic material is present 1) in sufficient quantity and 2) at a sufficient macrodomain size for efficient hysteresis augmentation to occur (including 0.5–2 micron particle diameters). Because the carrier/polyatomic complex agents and ion-cluster agents described in the preceding Examples have the properties of markedly improved selectivity and dose of tumor localization, retention in the viable (perfused) subregions of tumor, and improved tumor-cell uptake, it will be understood by those skilled in the art that these carrier/polyatomic complex and ion-cluster agents can be of significant benefit in augmenting the homogeneity, magnitude and tumor-cell selectivity of hysteresis heating induced by oscillating magnetic fields, provided that the associated superparamagnetic agents (which may be associated by conjugation, ion-pairing, or encapsulation) become concentrated as adequately sized macrodomains (of at least about 0.5 micron) in the target sites or cells. Histologic staining for cisplatin (per Example 7) of the VX2 rabbit carcinomas which were perfused with heparin-coated cisplatin-hydroxyethyl starch small microspheres (of 0.1–0.8 micron diameters), documented that many of the tumor cells in the target region addressed by selective arterial perfusion, stained intracellularly in a punctate pattern, wherein the diameters of punctate staining positivity ranged from 0.1 to 0.8 micron (=the diameters of the original particles). Importantly, high (including about 0.2 molar) intracellular concentrations of cisplatin were achieved in the VX2 carcinoma cells in vivo (see Example 8). The combination of these high levels plus intracellular aggregation were achieved by administering the cisplatin formulated as a heparin-coated microparticle. This documents the type and extent of intracellular accumulation and aggregation of superparamagnetics which can be achieved and are potentially useful in locally amplifying exogenous hysteresis heating. Notably, aggregated staining was absent following intraarterial perfusion of standard (soluble, low-molecular-weight) cisplatin. Hence, in the present example, heparin-coated $Cr_4S(O_2CCH_3)_8(H_2O)_4^{+2}$ hydroxyethyl starch small microspheres of 0.1 to 0.8 micron and intermediate-sized microspheres of 0.8-3.0 micron diameters, when administered intraarterially, are useful as amplifiers of hysteresis heating, and therefore as inducers of augmented cell death in vivo.

EXAMPLE 15

Novel Glycine-Substituted Polyatomic Cr Complex

Figure 5A:
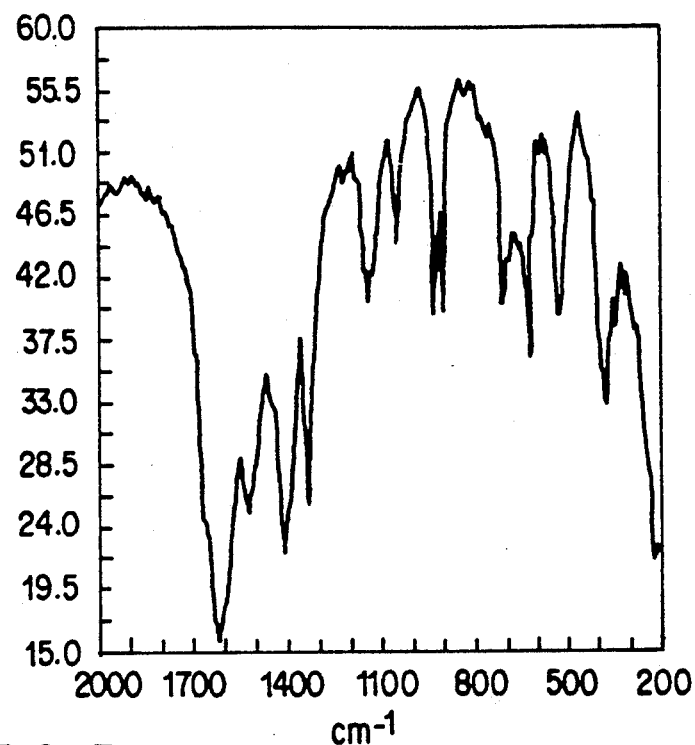
FIGS. 5A–5E show infrared data pertinent to the fabrication of a further alternative superparamagnetic complex, which can be used instead of that shown in FIG. 1.
Figure 5B:
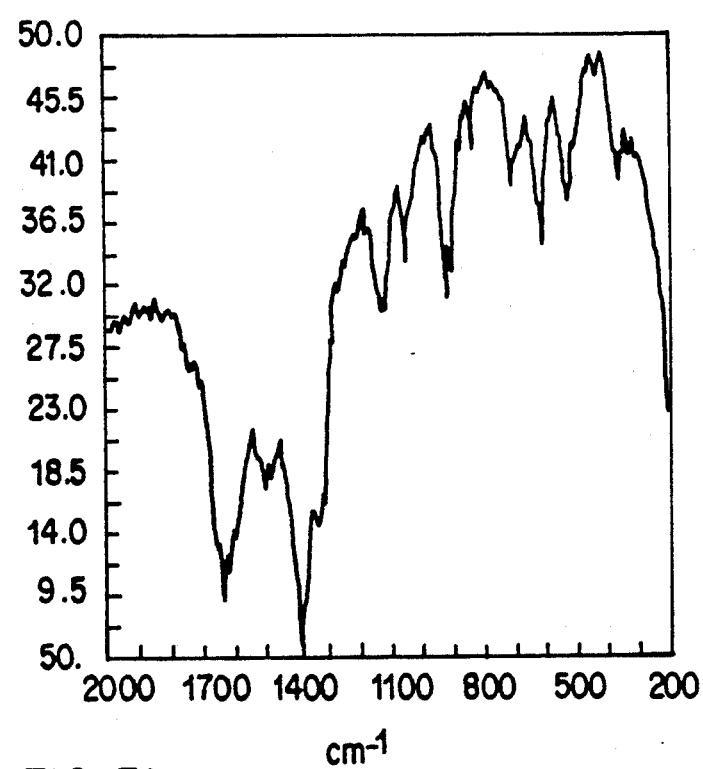
Figure 5C:
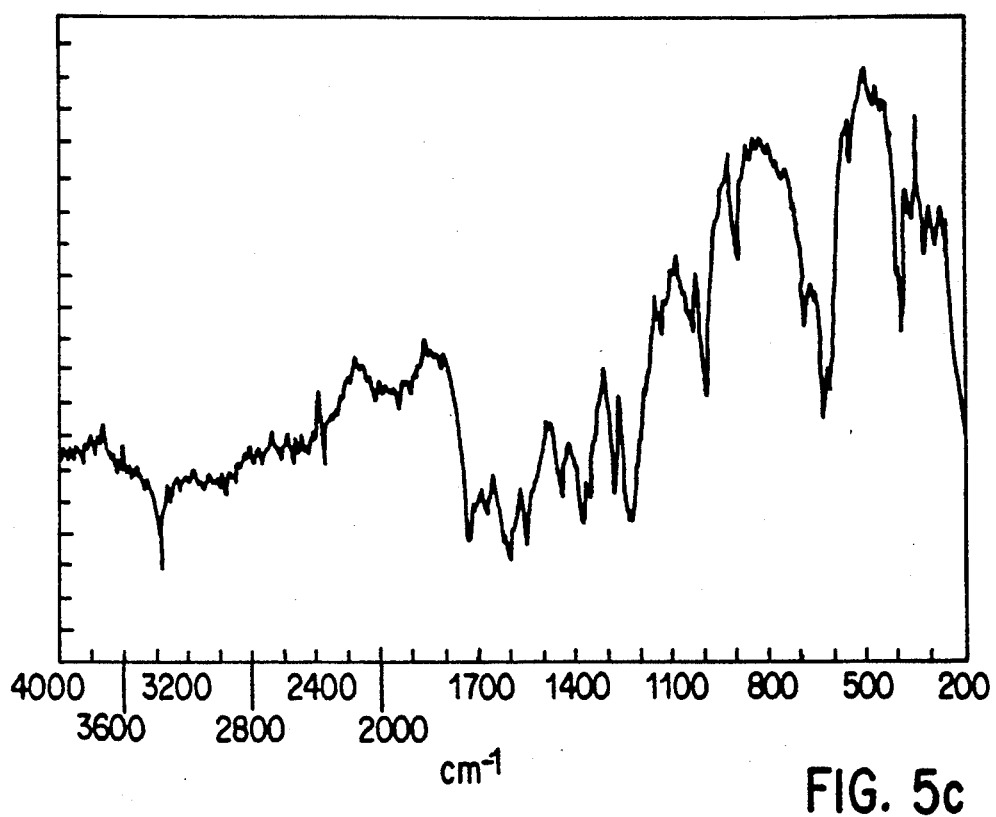
Figure 5D:
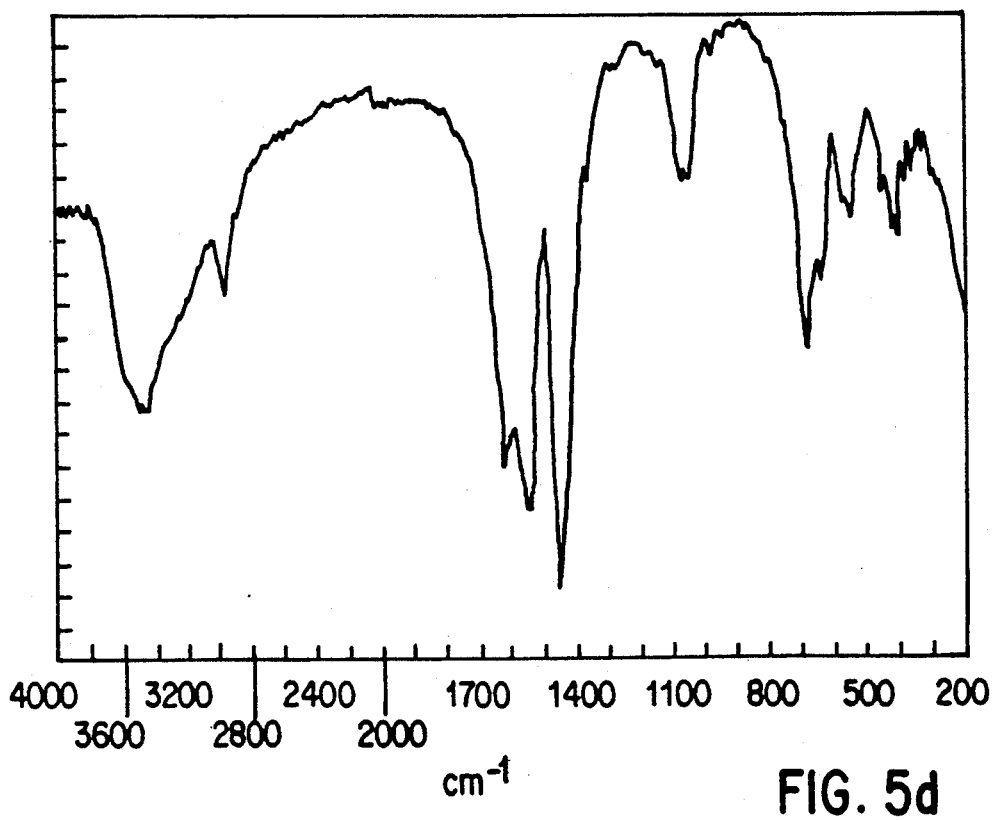
Figure 5E:
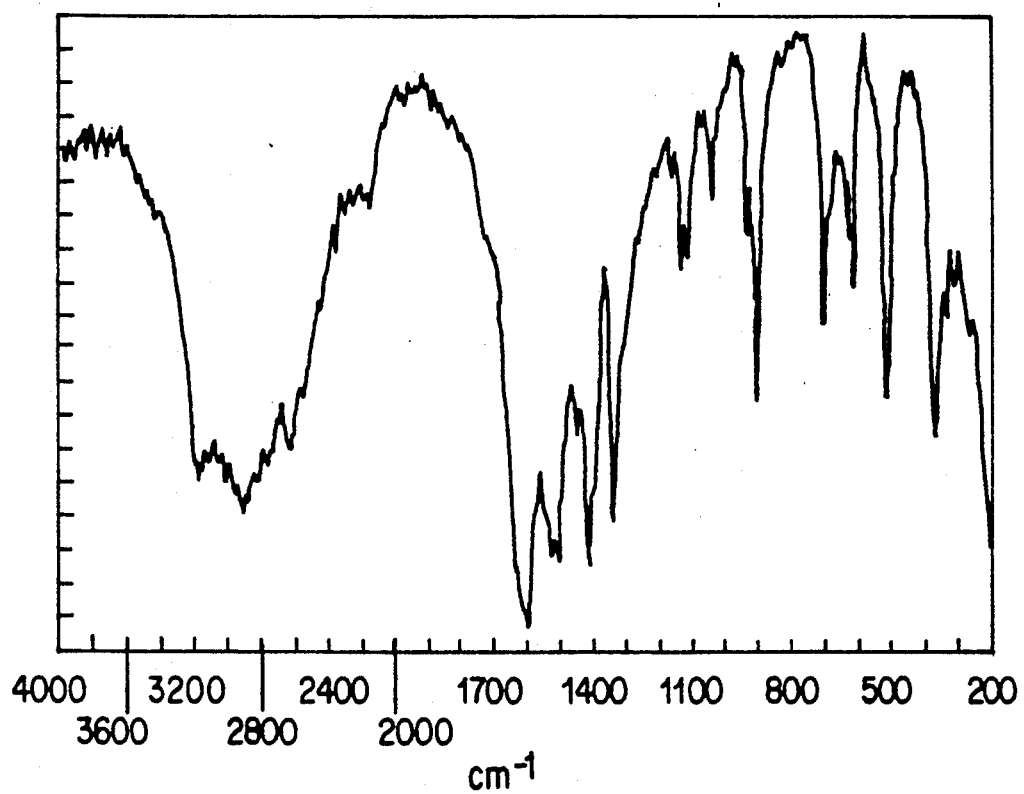

The substrate, $Cr_4S(O_2CCH_3)_8(H_2O)_4$, was prepared as described by A. Bino et al. (*Science*, Vol. 241, pp. 1479-1482, Sept. 16, 1988). This was added at 0.5 gm to 50 cc of acetic anhydride, followed by the addition of 0.1 gm of glycine. The mixture was refluxed at 142 degrees C. for 4 hours, resulting in a yellow-green solution which was poured while still hot into cold water. Evaporation of the solvent gave yellow crystals, which, when recrystallized, gave an infrared (IR) spectrum indicative of glycine substitution for some of the acetate bridging groups, and retention of Cr-O and Cr-S bonds (FIG. 5C, with FIGS. 5D and 5E representing the appropriate controls). Specifically, the IR bands around 1600 $cm^{-1}$ (FIG. 5C) are characteristic of ionized bidentate glycine, and the bands between 300 and 400 $cm^{-1}$ are also consistent with this. The additional bands between 300 and 400 $cm^{-1}$ are also consistent with the presence of Cr-O and Cr-S bonds. FIGS. 5A and 5B show the degradation controls wherein the $Cr_4S(O_2CCH_3)_8(H_2O)_4$ degrades to ionic chromium (by IR spectral criteria) when heated with glycine in an aqueous (protonating) solvent, water, for 4 hours at 92 degrees C. These results provide strong evidence for the formation of a novel polyatomic chromium-atom cluster compound of the general formula, $Cr_nS(O_2CCH_3)_x(Gly)_y(H_2O)_z$, wherein n is the number of Cr atoms greater than 1, x is the number of acetates between about 3 and 7, y is the number of glycines between about 1 and 5, and z is the number of loosely bound waters. The inclusion of bidentate glycine as a novel bridging ligand in the polyatomic chromium cluster provides a new reactive (charged) group for binding to carriers and renders the entire compound novel.

EXAMPLE 16

Novel Polyatomic Gadolinium Cluster Compound

Gadolinium chloride (3.7 gm, Alpha) and $Na_2S$ (2.4 gm, Sigma) were mixed in 25 cc of a 1:1 mixture of glacial acetic acid and acetic anhydride and refluxed at 138 degrees C. for 3 days. After removal of the dark red, gadolinium-negative filtrate, a lightly tan-colored precipitate was recovered which was qualitatively positive for gadolinium and which, after recrystallization, yielded a water-soluble water-stable compound whose IR spectrum was consistent with gadolinium acetate. Importantly, several additional bands were present in the carbonyl (ca. 1500 $cm^{-1}$) and C—O (ca. 1000 $cm^{-1}$) bond stretching wavelengths, which are strongly indicative of a polyatomic (polymeric) nature of this complex and, hence, indicative of a novel, gadolinium-containing, polyatomic complex for use with the disclosed carriers.

EXAMPLE 17

Formation of Stable Carrier/Polyatomic Metal Atom Complexes

Carboxymethyl dextran was obtained commercially and mixed with $Cr_4S(O_2CCH_3)_8(H_2O)_4$. The resulting complex had a T1 relativity (R1) 3 times greater than that of the simple chromium complex, indicative of paired-ion binding between the chromium complex and the carrier. Analogous mixtures were performed of $Cr_4S(O_2CCH_3)_8(H_2O)_4$ and (a) dicarboxyethyl dextran; (b) heparin; and (c) dextran sulfate. The resulting paired-ion complexes were stable to dialysis in 0.15 molar (isotonic) to 0.5 molar saline.

EXAMPLE 18

Stabilization of Chromium Complex and Complex-Carrier Associations, as Microparticles and Nanoparticles by Drying and Heating in Organic Solvents A. Chromium complex was obtained as in Example 11, dissolved in water at 25 mg/ml, Fraction A bovine lung heparin (6,000-8,000 MW) was added at a weight ratio of 4 parts heparin to 1 part chromium cluster, and this mixture was adjusted with NaOH to between about pH 5.5 and pH 7.0, and then magnetically stirred for 1 to 24 hours at 4C, with resultant formation (by interference light microscopy) of 1-4 um dark blue microparticles. This material was lyophilized for 24 hours in the presence and absence of mannitol plus dextrose in equimolar ratio, with the combined excipients equalling 300% by weight of the chromium complex-heparin microparticle weights. Upon resuspension of the lyophilized particles and examination by laser light scattering, only moderate transient physical stability of the particles was observed, with retention of nanoparticle and microsphere sizes for about 5 minutes.

Hence, these lyophilized materials were further resuspended respectively, in polyethylene glycol, glycerol, cottonseed oil, corn oil, acetone, acetone containing polyoxyethylene sorbitan mono-oleate at about 0.01 % to 25% by weight to the lyophilized materials, and these materials were dispersed in the organic phase either with low energy mixing or with high energy (pressure) dispersion methods, including rotor-stator dispersion and probe and bath sonification (=sonication). The materials were then heated, respectively at temperatures ranging from 110° C. to about 140° C., for between 3 and 5 min. For acetone formulations, heating were carried out under increased pressure in a microwave digestion bomb (Berghof America) with magnetic stirring. Depending on the type and extent of energy input and heating, this resulted in formation of blue nanoparticles of about 45 to 85 nanometers in mean diameter (Nicomp laser light scattering sizer), or blue microparticles of about 0.5 to 5.0 micrometers in mean diameter (Coulter Multisizer). Zeta potential measurements (Coulter Delsa 440) indicated that both the nanoparticles and microparticles had moderately negative surface charges of between about −40 and −50 millivolts. Ultraviolet absorbance measurements indicated that a majority of the characteristic 600 nm absorbance of chromium complex was retained for the particulate products obtained in all organic solvents, and that acetone-based solvents resulted in the highest preservation ratios to the native complex. The resulting particles were stable in distilled water and 55 dextrose in water, for intervals of between about 15 minutes and 48 hours after resuspension.

B. Chromium complex was obtained, dissolved, pH-adjusted, mixed with heparin and incubated with stirring as described in A. (above) but was not lyophilized. The complex-carrier adduct which formed was precipitated out of aqueous solution by stepwise addition of acetone to a final volume ratio of 2:1 (acetone:water). This material was resuspended by sonification in acetone containing polyoxyethylene sorbitan mono-oleate (at weight ratios as described in A., above) and the resuspended material was heated to between 110° C. and 140° C., under increased pressure in a microwave digestion bomb, as described in A., above). The resulting product was harvested by either air drying or lyophilization. Upon resuspension, the resulting nanospheres and microspheres retained their characteristic blue color and were stable to resuspension in water and 5% dextrose in water for up to 72 hours.

EXAMPLE 19

Stabilization of Chromium Complex and Complex-Carrier Associations, as Microparticles and Nanoparticles by Combination with Second Carrier (Matrix) Materials Fraction A beef-lung heparin of between about 6,000–10,000 MW (Hepar Corp.) was dissolved at 100 mg/ml in distilled water, and this was added, respectively, to protamine sulfate (Sigma) or hexadimethrine (Sigma) predissolved in water at 15 mg/ml, such that the weight ratios varied from 2% to 98% heparin (relative to the second carrier material). This resulted in stable, characteristically blue nanoparticles and microparticles, which retained their physical particulate stability (without heating) in water and in 5% dextrose in water, for intervals of up to and greater than 24 hours, for nanoparticles and microparticles, respectively. Protamine induced stability is preferred and gives physical stabilization for greater than 24 hours. The optimal ratio of protamine is between about 2.5% and 15% (w/w). Both the microparticles and nanoparticles could be harvested by centrifugation at 22,000×g for 10 minutes. The resulting nanoparticles so harvested, retain greater than about 60% of their starting magnetic potency, as evaluated by R1 relaxometry (IBM PC20 Relaxometer), and the microparticles retained greater than about 40% of the starting magnetic potency (same method). The differences in potency were consistent with greater availability of magnetic materials to diffusible water when these materials are comprised as smaller nanoparticles than as larger microparticles.

EXAMPLE 20

Testing for Exclusion of Cross-Linked and Microaggerated Species in the Soluble Polymeric Polyatomic Chromium Complex-Carrier Formulations The soluble polymeric intermediates and final formulations prepared in previous Examples 11, 12, 18 and 19 above, is tested for absence of cross-linking and microaggregation by ultrafiltration through a 10,000 MW cutoff filter (Amicon Corp.). In each case, less than about 5% of the total material of the soluble agents is retained above the filter.

EXAMPLE 21

Testing for Relative In Vitro Potencies of Bovine and Porcine Fraction A Heparins Fraction A heparins of between about 6,000 and 10,000 MW are obtained from bovine lung and porcine mucosal sources respectively (Hepar Corp.), these are added at increasing standard concentrations to Azure A dye (Sigma), and the resultant decrease in the characteristic UV absorbances at 620 nm are determined. The absorbances decrease linearly with heparin concentration over a range of about 0.1 to 10 ug/ml (and per assay tube), however, the slope for bovine lung Fraction A heparin is approximately 15 percent steeper than that for porcine mucosal Fraction A heparin. This provides in vitro correlative evidence that porcine mucosal heparin is less potent than bovine lung heparin in an in vitro binding assay (Azure A) which correlates empirically with both (published) differences in sulfation ratios (bovine being greater) and in vivo lung endothelial binding and targeting (see below).

EXAMPLE 22

Testing for Relative In Vivo Potencies of Bovine and Porcine Fraction A Heparins Fraction A bovine lung and porcine mucosal heparins of between about 6,000–10,000 MW are obtained as in Example 21, and are used to prepare microparticulate dispersions of the therapeutic agent, amphotericin B, for which a rapid high performance liquid chromatographic ultraviolet detection assay exists. The microparticulate dispersions of both heparin formulations have a mean size of about 5 to 8 micrometers, as assessed by interference light microscopy. At 1 hr following intravenous injection into Balb/c mice and homogenization/solubilization of the lungs for determination of lung amphotericin B levels, there is a substantial difference in the lung localization of amphotericin B core material which appears to result from differences in binding of the different heparin surface materials, as follows:

| Microparticles prepared from | Lung amphotericin B |
| --- | --- |
| 1. Bovine lung heparin | 27.6 ug/gm |
| 2. Porcine mucosal heparin | 6.0 ug/gm |

Although this result is obtained for core material other than the MRI enhancing agent material described in the current examples, to those skilled in the art, it indicates strongly that Fraction A heparin from bovine lung source is significantly more active for endothelial binding, transport and lung uptake than are the same Fraction obtained from porcine mucosal source, although it should be noted that porcine Fraction A heparin does indeed have endothelial binding/transport/uptake activity. This provides the initial in vivo basis for the present new, novel formulations for endothelial binding, transport and tissue uptake based on low molecular weight (less than about 10,000 MW) Fraction A heparins, and in particular on such fraction a heparin obtained from bovine lung source.

EXAMPLE 23

Imaging Data

Preparation of $(Cr_4S(O_2CCH_3)_8(H_2O)_4)$-heparin carrier (hereinafter "$Cr_4S$-heparin") for in vivo Magnetic Resonance imaging Two aliquots of the $Cr_4S$ ion cluster (37.5 mg each) were dissolved in 1 ml (each) of 5% dextrose in water. To the first aliquot was added 187.5 mg of dextran sulfate carrier (8000 Daltons); and to the second aliquot was added 187.5 mg of beef-lung heparin carrier (ca. 6,000–10,000 MW Daltons). Each aliquot (mixture) was tested for stability of $Cr_4S$-to-carrier binding, by nitrogen pressure ultrafiltration through an (Amicon Corporation) YM3 (3,000-Dalton cutoff) filter, followed by washing with 5% dextrose in water. Approximately 75% retention of the (intensely blue-colored) $Cr_4S$ ion cluster above the filter (i.e. in the retentate of more than 3,000 Dalton m.w.) was achieved by the heparin carrier. This indicated stable complexation binding of the $Cr_4S$ ion to heparin in the presence of 834 milliosmolar dextrose (equivalent to 0.42 M NaCl). Hence, the $Cr_4S$-heparin agent remained stably bound (complexed) under conditions equivalent to severe pathologic hyperglycemia (almost incompatible with life) and under conditions of lethal hypernatremia. Retention of $Cr_4S$ above the filter was also observed with the dextran sulfate carrier, but was not as complete as in the presence of heparin. This partial retention in the presence of dextran sulfate carrier may be due to the close proximity of the combined molecular weight of $Cr_4S$-dextran sulfate carrier (ca. 10000 Daltons) to the retention cutoff value of the YM3 filter (3,000 Daltons).

Acute Toxicity testing in vivo

The $Cr_4S$-heparin preparation (prepared as described in the preceding paragraph) was injected as an intravenous bolus into male CBA/Ln mice at ca. 3000 mg/kg, and the animals were observed for signs of acute toxicity. The animals tolerated this dose of the preparation well immediately after injection, and were also alive, active and gaining weight normally at 1 week post-injection.

Production of $Cr_4S$-heparin for in vivo imaging

The $Cr_4S$ ion cluster was allowed to stably complex with heparin at its stoichiometric binding ratio of ca. 30–35% (w/w) $Cr_4S$ to heparin (equivalent to about 5.4%–6.3% total chromium content (w/w to heparin). This was tested for T1 relaxivity (R1) using an IBM PC20 relaxometer (IR rf pulse sequence), and gave a 50% decrease in the water proton relaxation time at a concentration of ca. 0.33 to 1.0 mg/ml of total agent ($Cr_4S$-heparin).

In Vivo MRI of tumor-bearing and control mice

The $Cr_4S$-heparin MRI contrast agent (from the preceding paragraph) was injected at 0.08 mmol/kg (of $Cr_4S$ ion cluster) into Balb/c mice bearing a well-differentiated, slow-growing, malignant breast tumor induced in the mouse's lower right breast pad. Control animals consisted of uninjected normal mice and normal mice injected with $Cr_4S$-heparin.

Specifications of MR imager, imaging conditions, and image processing methods from MRI tests of murine breast tumor, enhanced with chromium ion cluster-heparin complex ($Cr_4S$-heparin)

Transaxial images were acquired simultaneously on three lightly anesthetized (i.p. pentobarbital) mice, using a standard clinical Diasonics whole-body, 0.35 Tesla MR imager, with the three mice oriented in the prone position, facing forward in the magnet and located centrally within a 20-cm radio frequency coil (standard knee coil). High resolution images were acquired over 2.6 minute intervals, both precontrast and at several postcontrast times between 10 and 30 minutes, at an in-plane resolution of 0.9×0.9 mm and a slice thickness of 5 mm. Five contiguous slices were acquired and the optimal slice photographed for maximal cross-sectional assessments of tumor, liver and kidney.

A pulse-sequence optimization program was run on the mice in the region of tumor, ranging from T1-weighted (TR=125 msec) to T2-weighted (TR=1800 msec) spin-echo sequences. The optimal spin-echo conditions were: TR of between 250 msec and 500 msec at an echo time (TE) of 40 msec. Based on these results, a spin-echo pulse sequence was used of TR=325 msec and TR=40 msec. (Note that optimization of contrast enhancement under these T1-weighted spin-echo conditions has two important implications: 1) the $Cr_4S$-heparin agent behaves as a "T1" contrast agent; and 2) the $Cr_4S$-heparin agent is optimal for use with the more commonly employed, higher signal-to-noise clinical T1 pulse sequences.

Quantitative changes in tumor image intensities in vivo, at 10 and 30 minutes after intravenous injection of contrast agent ($Cr_4S$-heparin) at a dose of 0.08 mmol/kg (based on chromium-ion complex) were assessed in the following standard fashion:

1) The average image intensity of central tumor region was acquired (from 64–80 image pixels each) by drawing a cursor box around the comparable central regions of tumor at precontrast, 10-minute post-contrast and 30-minute postcontrast times. (NOTE: Refer to the second, lighter grey scale, 35-mm projection slide of tumor for the exact positioning of the cursor box (this appears as a dark, irregular, rectangular-oblique line over the right-hand flank of the mouse, directly below the bright external stick-marker which was taped to the mouse skin at the site of the tumor. See FIG. 6 and Table 2.)

2) The average image intensity of vertebral muscle was acquired identically (from 20–64 image pixels each). (Note: in FIG. 6, note the positioning of the smaller, dark square cursor boxes located centrally and at the top (dorsum) of each mouse (in the pre, 10-min postcontrast and 30-min postcontrast panels). See FIG. 6 and Table 2.)

3) Any potential artifacts in the postcontrast intensity of breast tumor which might be introduced by changes in the overall intensities of the postcontrast versus precontrast images are corrected (normalized) by the standard method (accepted experimentally and clinically), of forming the mathematical ratio of tumor-to-vertebral muscle image intensities at each imaging time (pre, 10-min post, and 30-min post). (See Table 3, which is derived from Table 2.)

Specifications of NMR Relaxometer, relaxation conditions, and data acquisition for in vitro confirmation of tumor T1 relaxation time and pre-to-postcontrast differences in liver and kidney T1 relaxation times At 40 minutes after injection of contrast agent, the exact animals imaged above were sacrificed, the tumor and organs removed and the T1 relaxation times were determined using an IBM PC20 Relaxometer (operating at 20 MHz), using a T1 inversion-recovery, 180 degrees+90 degrees radiofrequency pulse sequence. (See Table 4.)

The raw data are expressed as the means of 3 to 5 individual measurements made on each organ (or tumor). the processed data are expressed as the "percent of Control" organ T1 (which is the "B" Uninjected Control animal). (Please note: A difference of about ±7% is significant for each value. Hence, the decreases in kidney T1's are highly significant for both of the injected animals ("A" and "C"), but the liver T1's of these same animals are not significantly different from the uninjected control animal ("B"). Note also: Changes in the in vitro T1 relaxation times are inversely related to changes in the in vivo image intensities (enhancement of organs and tumor) at small to moderate percentage changes where T1 effects predominate and T2 effects are minor (typically at T1 percentage decreases less than about 30–40%).

In Vivo Tumor Imaging Results

Figure 6A:
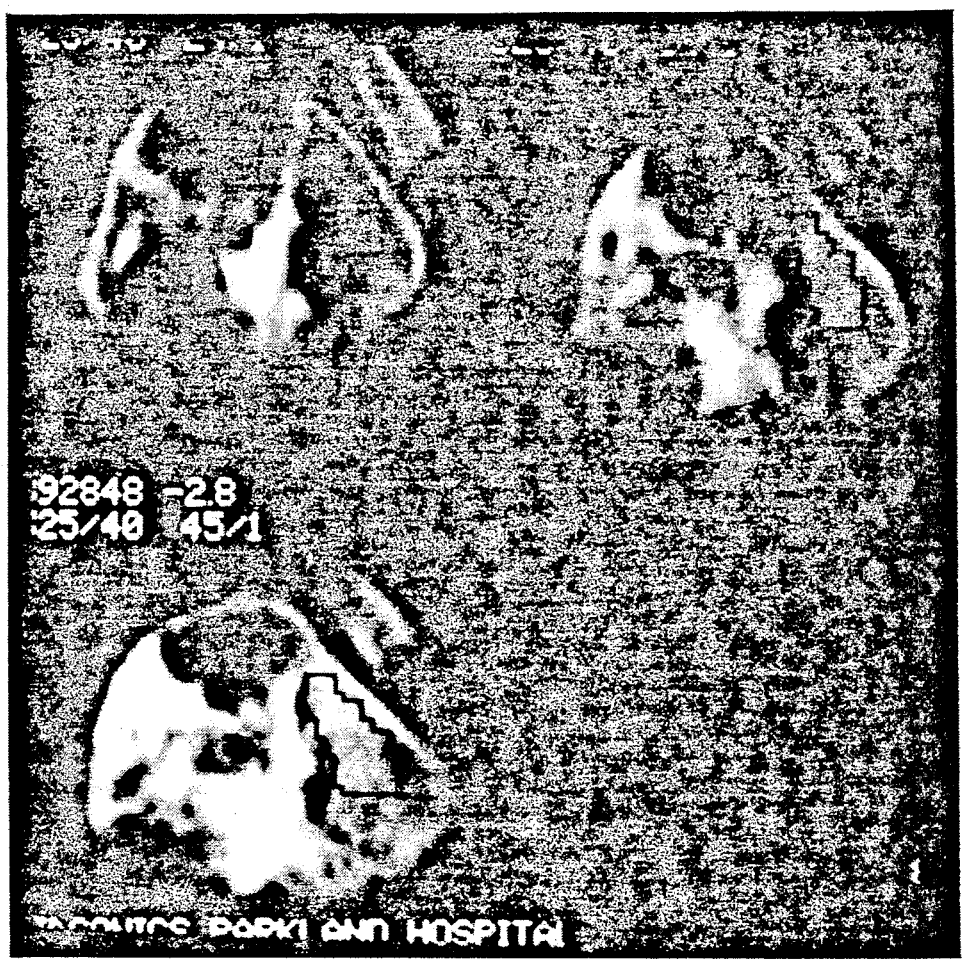
FIG. 6A shows in vivo magnetic-resonance imaging of solid tumors in tumor-bearing mice, recorded in accordance with a sample embodiment of the novel imaging methods set forth herein.
Figure 6B:
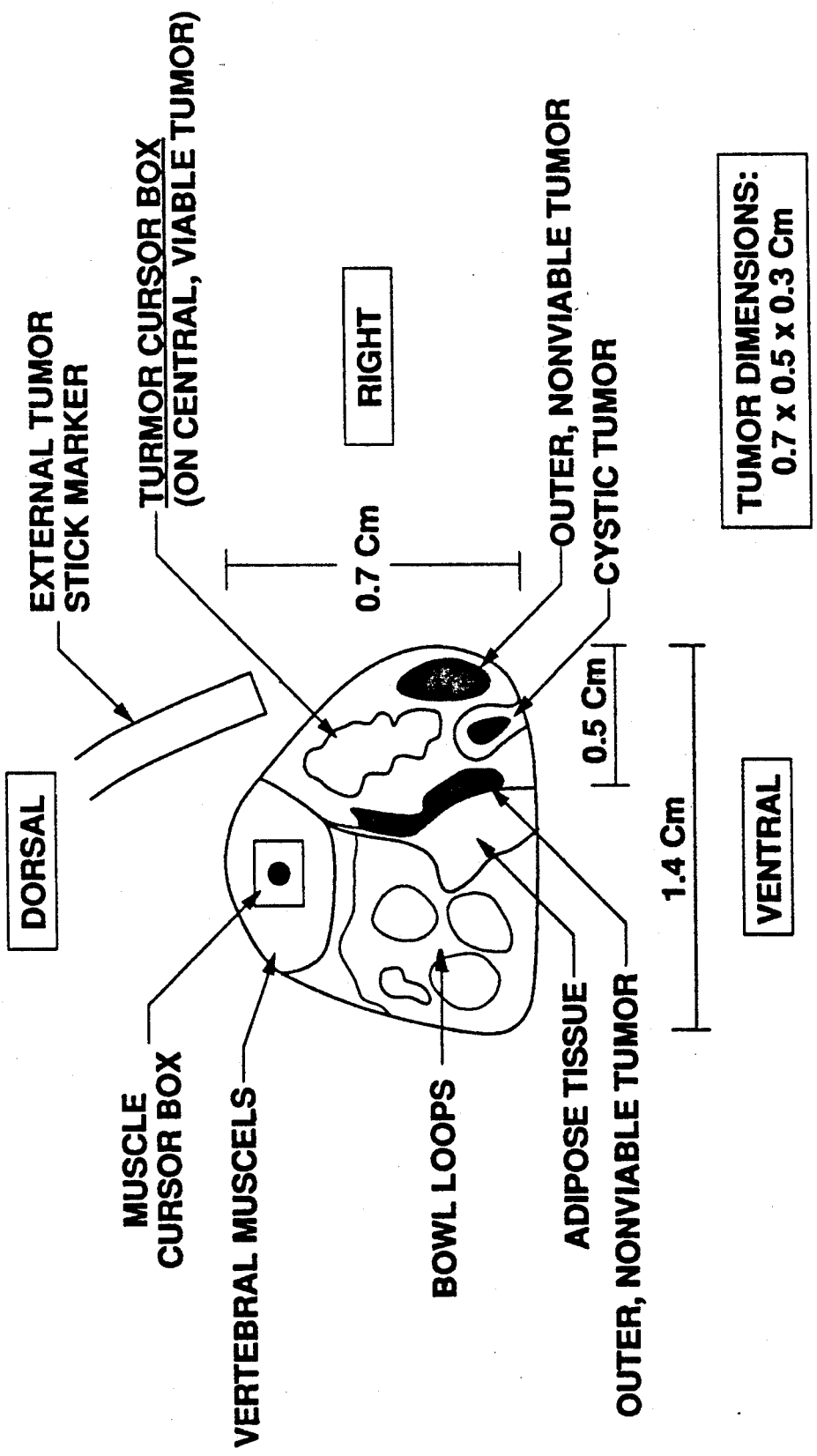
FIG. 6B is a corresponding sketch to assist in the interpretation of that image.

FIG. 6, which shows tumor mass in right flank, with the label of image slice "45/1" on the lower left-hand image panel, and the stick marker located just dorsal to the tumor and cursor boxes located centrally within tumor mass (at image right) and centrally within vertebral muscle (at image top). (The tumor map further clarifies orientation and dimensions.)

1) Precontrast: The entire tumor mass has an intermediate (grey) appearance which is relatively homogeneous. (Refer to Table 2 for the absolute values of tumor and muscle intensity.) The ratio of tumor/muscle intensity (within the cursor boxes) is 1.51/1. (SEE Table 3.)

2) 10 minutes Postcontrast: The central core of the tumor mass (circumscribed by the cursor box) has increased markedly in absolute intensity, whereas the vertebral muscle has not (Table 2). The increment in central tumor intensity is such that the tumor/muscle ratio has increased to 1.98 (or by 31%). Substantial tumor architecture is now seen which was not visualized in the precontrast image (with this T1-weighted sequence—TR=325 msec; TE=40 msec) or any other of the pulse sequence tested - see above). The outer rim of tumor, both medial to the bottom of the cursor box, and at the lateral right border of tumor (just to the right of the bottom of the cursor box) are significantly darker than the central core. Also, a darker cystic structure with a surrounding brighter rim is present immediately below (ventral to) the bottom of the cursor box. CORRELATION: On gross histologic examination, the three darker regions corresponded to necrotic regions of tumor, and the bright central regions corresponded to viable tumor with more extensive microvascularization.

3) 30 minutes Postcontrast: The same enhancement of tumor subregions is observed as at 10 minutes postcontrast. NOTE: The overall image intensity is slightly brighter at 30 minutes versus 10 minutes; however, as assessed by muscle intensity ratios, the muscle increment at 30 minutes is very slight (4% brighter based on absolute muscle intensity ratios of 3003/2896). Notice also that the external stick probe is visually of about the same intensity from precontrast to 30 minutes postcontrast.

NOTE: By visual inspection, the range of image pixel intensities in the central core of tumor (cursor boxes) is narrower at 10 minutes postcontrast than at 30 minutes postcontrast. This correlates with a lower standard deviation of tumor image intensity by quantitative pixel analysis at 10 minutes postcontrast (Table 2, line 2) than at 30 minutes postcontrast (Table 2, line 3).

Renal and Hepatic Data

Figure 7A:
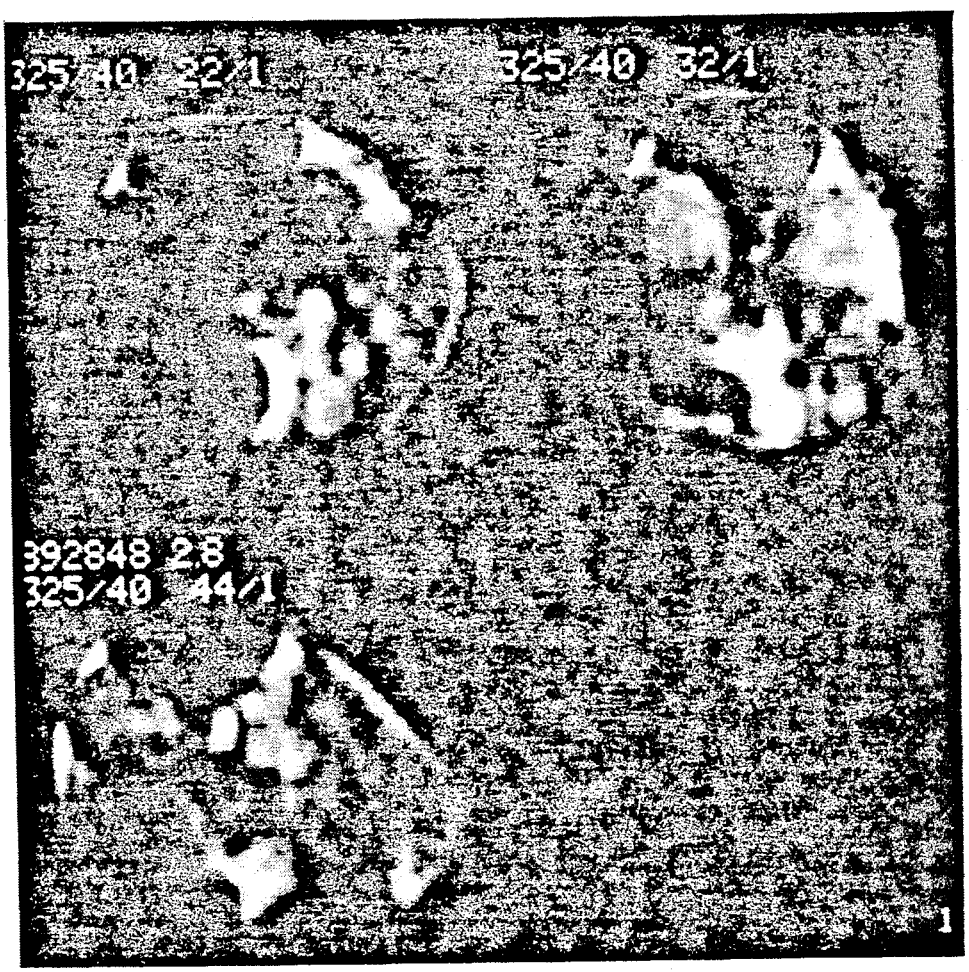
FIG. 7A is a magnetic-resonance image of kidneys in the mice of FIG. 6A.
Figure 7B:
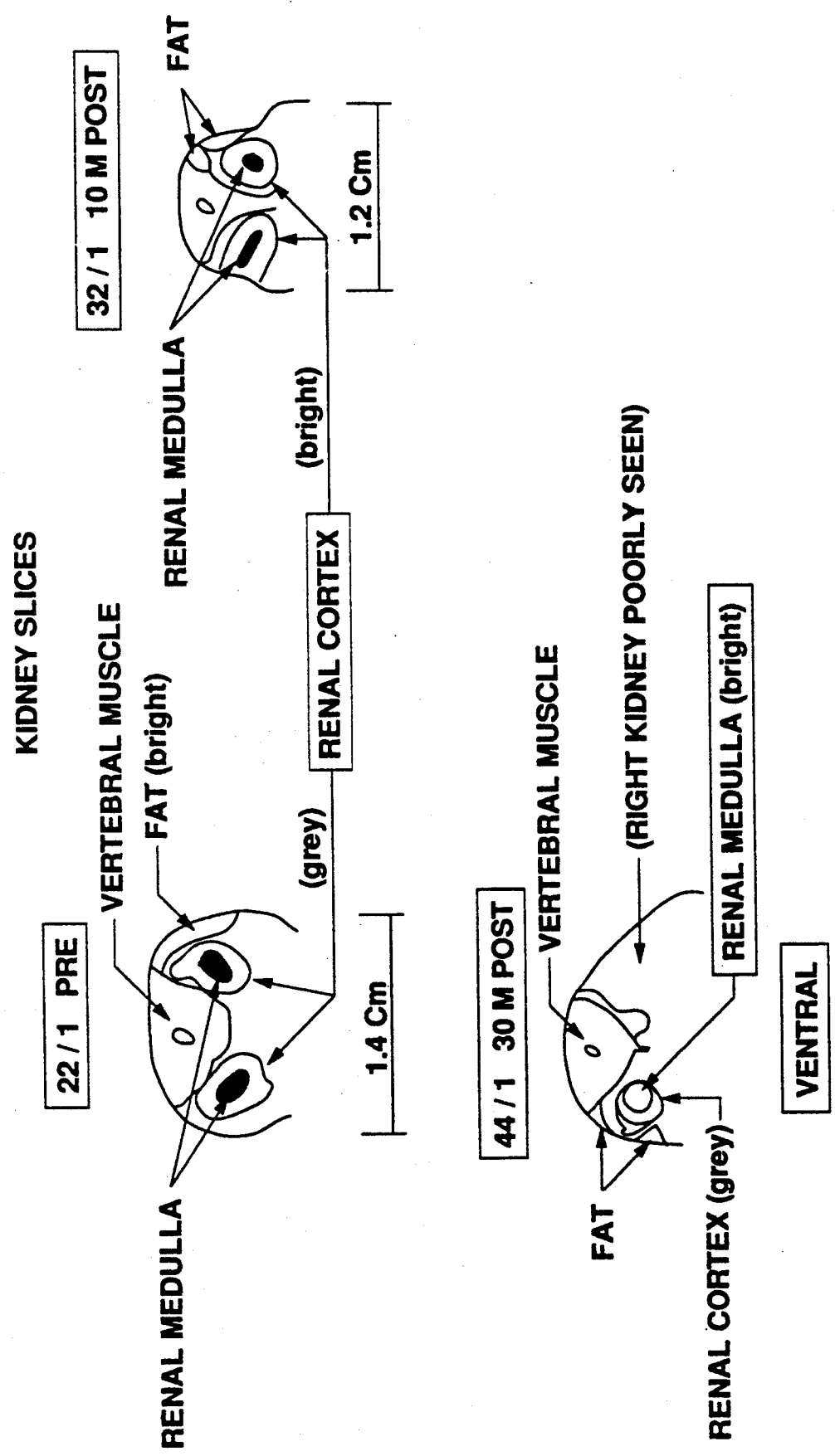
FIG. 7B is a corresponding sketch to assist in the interpretation of that image.

FIG. 7 shows the renal image slices, marked 22/1, 32/1 and 44/1, respectively at the precontrast, 10-min postcontrast, and 30-min postcontrast intervals.

1) Precontrast: The faint outlines of both renal cortices appear as intermediate (grey) intensity oval outlines which are located immediately ventral and slightly lateral to the dorsal vertebral muscle, and which circumscribe the darker (black) central renal medullas.

2) 10 minutes Postcontrast: The image intensities of renal cortical regions are markedly increased in intensity, with the medullary regions being relatively darker although still absolutely increased.

3) 30 minutes Postcontrast: The image intensity of left renal cortex (the left kidney is the only one which is clearly seen in this postcontrast image) has decreased markedly relative to the 10-minute postcontrast time, but remains slightly brighter than the precontrast intensity. conversely, the left renal medulla (central region of left kidney) is quite intense, indicative of continued contrast accumulation in the renal collecting system.

Figure 8A:
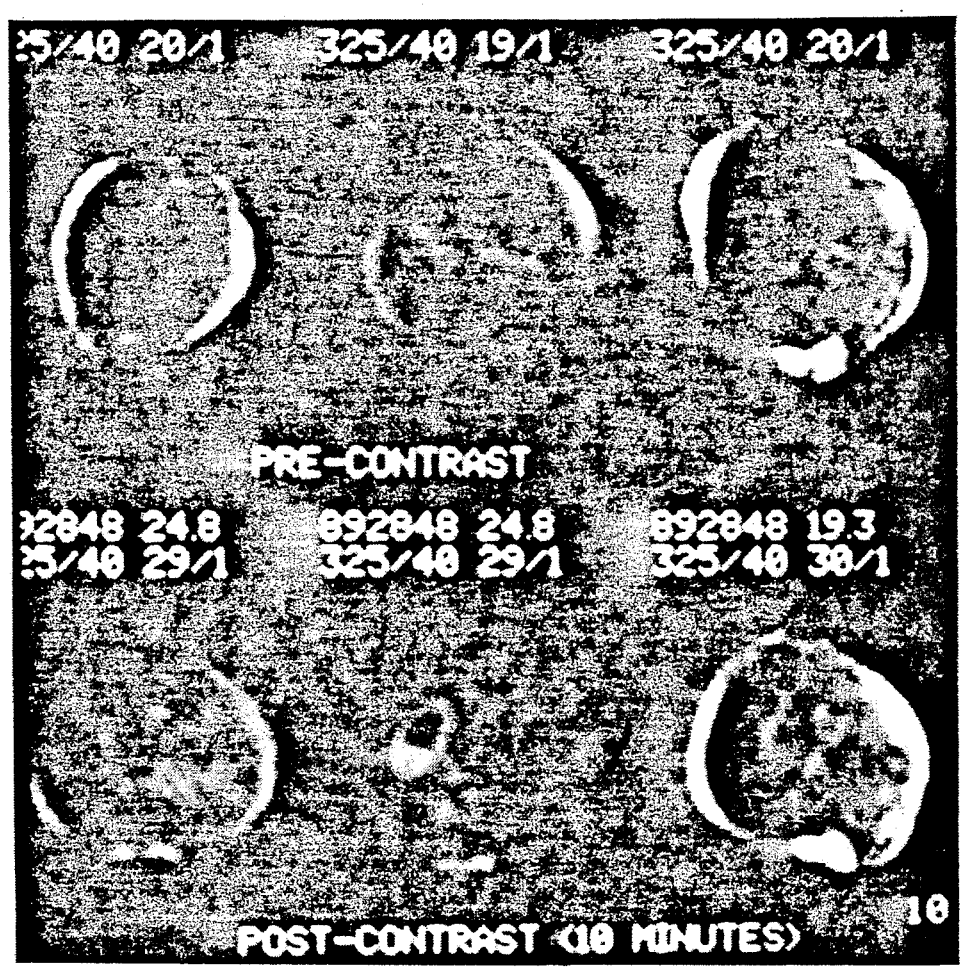
FIG. 8A is a magnetic-resonance image of livers in the mice of FIG. 6A.
Figure 8B:
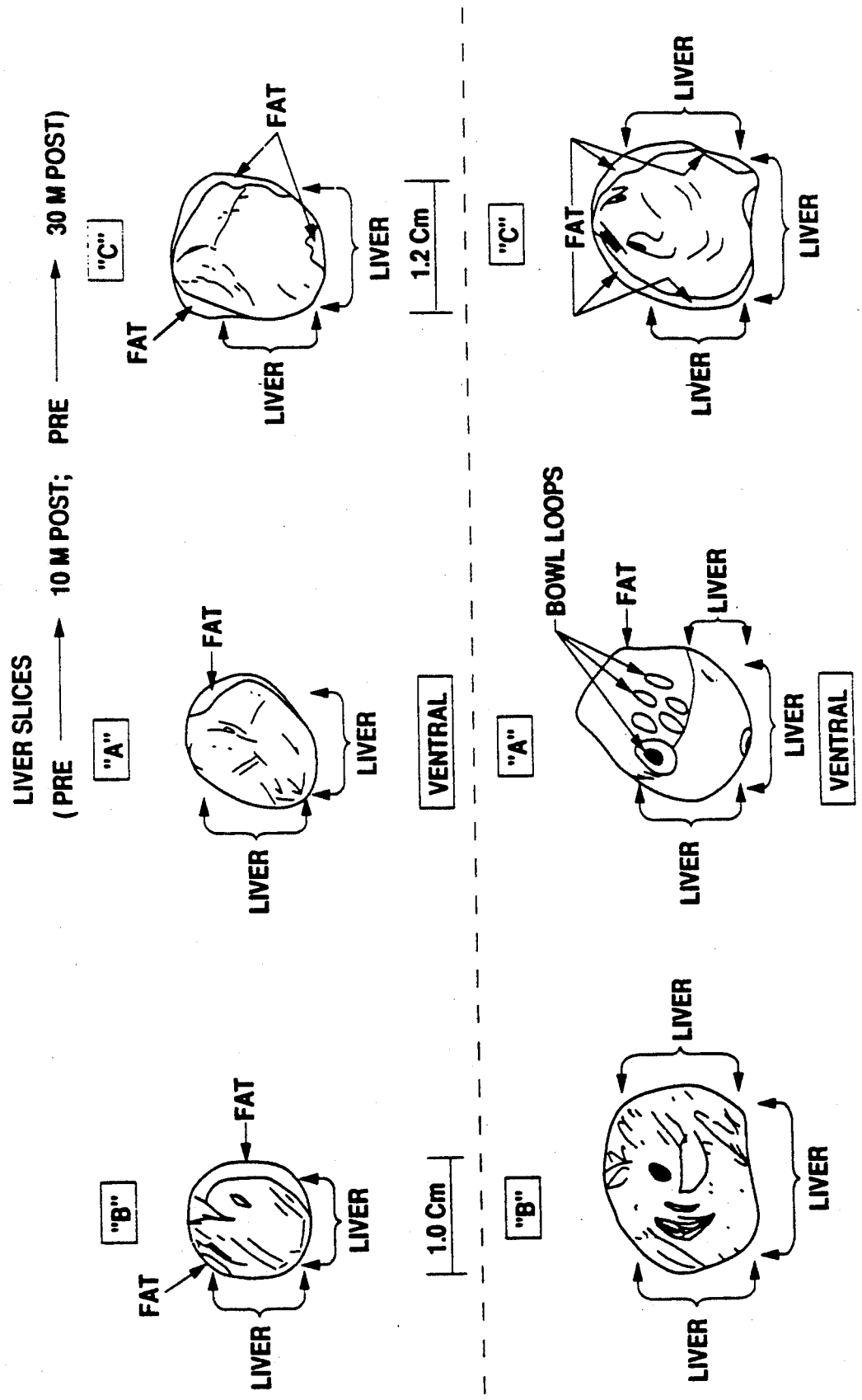
FIG. 8B is a corresponding sketch to assist in the interpretation of that image.

FIG. 8 shows a panel of 6 liver slices—3 top and 3 bottom—at precontrast, and 10-minute postcontrast intervals.)

1) Precontrast livers are viewed in the upper row images as relatively homogeneous, intermediate-intensity (grey) masses which fill almost the entire internal abdominal volume of each mouse. The darker tube-shaped regions are larger hepatic veins and the occasional brighter regions are hepatic septae and omental fat due to caudal volume averaging (see below). The liver image of the left-hand mouse (upper row) is positioned slightly cephalad (superior) to the optimal position for liver imaging, as indicated by the slight decrease in body width. The darker intensity of this precontrast image (relative to the other five livers) is due to slight partial volume averaging with the adjacent lung fields (which, if imaged alone, would appear black).

2) Postcontrast livers of the identical animals appear in the bottom row, as follows:
  a) left-hand animal (mouse "B") is contrast-injected ($Cr_4$Sheparin at 0.08 mmol of $Cr_4$S/kg) normal (nontumor) control mouse.
  b) middle animal (mouse "A") is an uninjected normal control mouse.
  c) right-hand animal (mouse "C") is a tumor mouse injected with 0.08 mmol/kg of $Cr_4$S-heparin contrast agent.

NOTE: In an optimal 5 mm-thick image slice, the liver appears relatively homogeneous and of intermediate (grey) image intensity. At both 10-minute (shown) and 30-minute (not shown) postcontrast times, dark loop densities (bowl loops) and occasional small bright nodules and ring structures (omental fat) are seen in the liver slice of the middle "A" mouse. This is not due to contrast agent (none was injected into this mouse), but is due, instead, to slight caudal mispositioning (and, hence, volume averaging) of the liver image slice. A similar but less prominent artifact is present in the left-hand "B" mouse. Minor volume averaging of this type is usually present in a multi-animal experiment because the mouse liver is only about 5 mm in average height.

OVERALL RESULT: There is no significant image enhancement of liver in either of the injected mice (left "B"; or right "C") at either earlier (10-minute—shown) or later (30-minute—not shown) postcontrast times at which images were acquired.

Preliminary Conclusions

Based on the further experimental data just described, some additional conclusions appear to be justified:

1) Enhancement of a difficult (relatively differentiated) breast carcinoma occurs acutely (10 minutes) after a low (0.08 mmol/kg) dose of the $Cr_4S$-ion cluster-heparin complex.

2) This enhancement persists for an extended, 30-minute postcontrast interval and is not significantly decreased at 30 minutes.

NOTE: This preservation of postcontrast enhancement is markedly longer than the contrast enhancement resulting from Gd-DTPA dimeglumine (MAGNEVIST, Schering AG-Berlex) which undergoes almost complete fading (tumor clearance) by 30 minutes postcontrast.

3) Maximal image enhancement occurs in functionally viable (perfused) tumor subregions; and minimal enhancement occurs in necrotic subregions.

4) Systemic clearance of the $Cr_4S$-heparin MRI contrast agent is predominantly by the renal route and occurs relatively quickly (first, major component requires about 30 minutes—as evidenced by the brightening and then fading of the renal cortex, with continued moderate contrast intensity in the renal medulla at 30 minutes).

5) Importantly, no major acute uptake occurs into NORMAL liver during optimal postcontrast imaging intervals.

Interpretation and Implications.

1) Although the $Cr_4S$-heparin contrast agent contains four Cr ions per ion complex in a superparamagnetic orientation (and, hence, exhibits intracomplex magnetic coupling), in vivo pulse-sequence tests indicate that this contrast agent acts as a potent T1 agent. in vivo dose-efficacy results indicate that this is a highly potent agent. This result suggests that the agent has a more selective initial biodistribution compared to the existing small-molecular contrast agents (e.g., MAGNEVIST and Gd-DTPA, which exchange freely into ca. 35% of total body water and into most of the extracellular fluid, ECF).

2) Following i.v. injection, the $Cr_4S$-heparin agent becomes sequestered rapidly in tumor interstitium but not in normal liver interstitium or parenchyma. This unique property provides for optimal body (as well as brain) imaging of tumors (including tumor within the liver) as well as potentially other body lesions (hepatitis and inflammatory/infectious lesions).

3) Tumor retention of contrast agent is prolonged relative to the rapid blood clearance (inferred from the rapid renal cortical clearance phase).

In Vitro T1 Measurements

In vitro measurements were also performed on the organs imaged in the foregoing in vivo imaging experiment, with results as shown in Table 4.

The T1 changes of organs freshly excised at 40 minutes postcontrast (i.v. injection) from the animals imaged above, indicate significant decreases in the T1's of kidneys for the contrast-injected "A" and "C" animals (relative to the uninjected "B" animal). However, they show no significant decreases in the T1's of livers for the injected versus uninjected animals.

These results confirm the in vivo imaging results and establish that the major route of clearance is renal. They also confirm that there is no significant acute clearance by normal liver.

Similarities and Differences between Agents
Similarities of $Cr_4S$-Heparin and Gd-DTPA-dextran 1. Increased chemical potency (increased proton T1 relaxivity) due to slower rotational correlation time of polymeric versus small molecular contrast agents 2. Restricted initial biodistribution of polymeric contrast agents in vivo (in ca. 10% of body water versus 35% for freely ECF-exchanging, small molecular agents)
   a. increased in vivo potency
   b. potentially decreased in vivo toxicity 3. Advantage of being strong T1-relaxation agents in combination with the newer, more heavily T1-weighted MRI pulse sequences 4 Improved imaging of tumors in body and brain sites, due to improved selectivity of tumor uptake
   a. avoidance of acute uptake by normal liver (unlike standard, small contrast agents)

5. Improved detection of small tumor masses (due to increased contrast gradient at tumor margins)

6. Prolonged enhancement of tumors prior to contrast fading
   a. patient premedication outside of imaging room
   b. acquisition of multiple, sequential images with different pulse sequences prior to contrast fading
   c. imaging of multiple body regions after a single dose 7. Essentially complete aqueous solubility 8. Rapid clearance by the renal route 9. Isosmotic at typical injection concentrations and doses 10. Identification and differentiation of functional tumor subregions (viable versus nonviable), due to slower interstitial diffusion of these polymeric agents relative to standard small molecular agents
   a improved assessment of viable tumor mass
   b. noninvasive method for monitoring acute tumor-treatment effects.

Advantages of $Cr_4S$-Heparin over Gd-DTPA-dextran

1. $Cr_4S$-beef-lung Fraction A heparin has a lower molecular weight less than about 10,000 Daltons) than Gd-DTPA-dextran 70 (ca. 46,000 Daltons). (This may lead to improved tumor ACCESS of $Cr_4S$-heparin.)

2 Each $Cr_4S$ ion cluster of $Cr_4S$-heparin contains 4 chromium ions oriented so as to produce magnetic coupling and result in a "superparamagnetic" ion complex which is ca. 1.7 times more potent than a single gadolinium ion (due to the resulting 12 unpaired electrons of $Cr_4S$ versus only 7 for gadolinium.)

3. For $Cr_4S$, increased loading of strongly paramagnetic centers per unit length and weight of polymeric carrier (due to increased net paramagnetism in each polyatomic ion-cluster side group relative to each gadolinium-DTPA side group.

4. The heparin carrier has been established histologically (not shown) to be transported inside tumor cells, rather than just into the extracellular space surrounding tumor cells (this may contribute to prolonged contrast enhancement).

5. Possibly more rapid renal clearance of $Cr_4S$-heparin due to smaller size of polymeric carrier.

6. Possibly increased uptake and more prolonged retention of $Cr_4S$-heparin in tumors due to:
   a. selective active uptake of heparin across lesional (tumor) endothelium; and
   b. selective binding of heparin carrier to tissue matrix components of lesional (tumor) sites, including: fibronectin split products, laminin, collagen fragments, endogenous heparin sulfates and other matrix substances exposed in disease.

NOTE: Heparin which is fully complexed to $Cr_4S$ does not produce significant in vivo anticoagulation (as assessed by the glass-induced clotting time of whole murine blood after intravenous administration of ca. 3 times the effective imaging dose).

TABLE 2

Absolute Intensities* of Murine Breast Tumor and Vertebral Muscle in MR Images (in vivo)

| Group | | Intensity of Tumor* (Mean ± 1 SD) | Intensity of Muscle* (Mean ± 1 SD) |
|---|---|---|---|
| 1. | Precontrast | 4367 ± 553 | 2896 ± 589 |
| 2. | Postcontrast 10 minutes | 5723 ± 674 | 2885 ± 631 |
| 3. | Postcontrast 30 minutes | 5648 ± 801 | 3003 ± 436 |

*In arbitrary units, based on 20 to 80 image pixels

TABLE 3

Relative Intensity of Murine Breast Tumor in MR Images (in vivo)*

| Group | | Intensity of Tumor/Muscle | Increment (%) |
|---|---|---|---|
| 1. | Precontrast | 1.51 | — |
| 2. | Postcontrast 10 minutes | 1.98 | 31 |
| 3. | Postcontrast 30 minutes | 1.88 | 25 |

*Data are derived from Table 2 and are based on means of 20 to 80 image pixels

TABLE 4

T1 Relaxation Times of Freshly Excised Organs 40 Minutes after Injection of Access MRI Contrast Agent

| Animal | Organ | T1 (msec)* | % of Control |
|---|---|---|---|
| A) Control, Injected | Kidney Liver | 268.5 336.0 | 73.2 95.3 |
| B) Control, Uninjected | Kidney Liver | 367 352.5 | Control Control |
| C) Tumor, Injected | Kidney Liver Tumor | 269 343 553 | 73.3 97.3 — |

*Data are means of 3 to 5 individual measurements

Further Modifications and Variations

It will be recognized by those skilled in the art that the innovative concepts disclosed in the present application can be applied in a wide variety of contexts. Moreover, the preferred implementation can be modified in a tremendous variety of ways. Accordingly, it should be understood that the modifications and variations suggested above are merely illustrative. These examples may help to show some of the scope of the inventive concepts, but these examples do not nearly exhaust the full scope of variations in the disclosed novel concepts.

For example, although the presently preferred embodiment is primarily directed to imaging, the selective transport advantages provided could also be used to enhance the performance of NMR spectroscopy of the human body if desired.

For another example, it is alternatively possible to combine a carrier group with a small therapeutic complex. Combinations of boron (or a boroleptic group which provides a site for boron), or of cis-platinum (more precisely, cis-dichlorodiamine platinum), with a carrier group like those described above may be advantageous. The active agent may be selected to provide chemotherapeutic impact, or to provide sensitization or augmentation for radiation treatment.

For one example, although the disclosed innovations are particularly advantageous in selective transport to tumor sites, they can also be adapted for use with a wide variety of other types of disease or pathology, to selectively address sites where "vascular-permeability-increased" tissue exists. For example, the disclosed innovations can be adapted for use in treatment or imaging (or fine-scale diagnosis) of arthritis, diabetic angiopathy, retinitis, transplantation rejection, or other inflammatory conditions.

Similarly, the disclosed innovative ideas can also be adapted for selectively imaging sclerotic tissue, and thus may be useful in dealing with conditions such as arteriosclerosis or multiple sclerosis.

For yet another example, the disclosed innovative ideas can also be used to monitor rates of drug arrival, release, or backdiffusion.

In a further alternative, synthetic polymers other than CARBETIMER TM could be used. CARBETIMER TM is a polyaldehyde/polyamine synthetic polymer, which provides useful transport characteristics as a carrier. Many other such synthetic polymers have been proposed, and could be used, if desired, as the polymer in the carrier.

It should also be noted that the carrier can be used either as a polymer or as a microsphere (or other supermolecular aggregation). Polymers are most preferably given a molecular weight in the range of less than about 10,000 Daltons, as described above; but larger polymer sizes may be advantageous for some applications. In particular, where the toxicity is very low (as with chromium), it may be advantageous to use a polymer whose molecular weight is above the renal clearance limit. In such cases, the resulting clearance time will permit the composition to be used as a "blood pool," where a low blood concentration is available over a long period of time to diffuse into a target site. (This may be particularly useful for therapeutic applications.)

Microspheres are even larger than the largest preferred polymer sizes. For example, a polymer of 200,000 Daltons molecular weight will have a typical maximum dimension of less than 12 nm, whereas a microsphere will have a diameter of 100 nm or more. The present invention may optionally be used with microspheres as large as 250 microns. (The larger microsphere sizes are primarily useful for embolization imaging of lung and tumor, and for imaging body cavities, such as lung, bladder, bowel, or central nervous system cavities.) Microspheres may include a surface coating which provides available reactive groups, such as hydroxyl, carbonyl, aldehyde, carboxylate, sulfate, phosphate and amine groups (singly or in combination), for binding to the complex being transported, whereas these reactive groups need not be present in the matrix of the microsphere. However, it should be noted that the polymers of the microsphere matrix should preferably be completely water-soluble, to facilitate clearance from the body.

It should also be noted that a composition of microspheres, with a diameter between about 0.1 micrometer and about 4.0 micrometers, and a polyatomic metal atom cluster which consists essentially of $(Cr_4S(O_2CCH_3)_8(H_2O)_4)^{+2}$ bound to diethylenetriaminepentaacetate-dextran, diethylenetriamine pentaacetatehydroxyethyl starch, heparin, dextran sulfate or pentosan polysulfate, is believed to be particularly advantageous for liver imaging.

A further point which should be noted is that carriers (such as dextran) have been ionically coupled to an active agent, to produce drug salts; but it has not been conventional to chelate an active agent to a carrier, as is disclosed in some of the innovative examples above. As the examples above show, this further innovative teaching is believed to provide significant advantages.

For superparamagnetic polyatomic structures, it should be noted that heteropolyatomic structures can be used to reduce the need for binding ligands. For example, it is known that vanadium, cobalt, or tungsten can be used as binding atoms to stabilize the relative positions of chromium atoms.

For another modification of the superparamagnetic polyatomic structures, it is expected that the central coordinating atom (which is sulfur in the $Cr_4S(O_2CCH_3)_8(H_2O)_4^{+2}$ example) could alternatively be tungsten, or even vanadium, molybdenum, cobalt, or other species.

In a further alternative, it has been found that transport of glycerol by a polymeric carrier actually increases the permeability of the vascular walls in the tumorous region. Thus, optionally, this effect can be used to further increase the selectivity of delivery of the desired agent.

Moreover, the varying requirements of various applications may imply a rebalancing of the various factors enumerated. For example, where it is desired to transport a metal ion which is very non-toxic, loose binding to the polymeric carrier may be perfectly acceptable. Conversely, in some cases covalent bonding may be particularly advantageous. Paired-ion embodiments may be advantageous for improved renal excretion. Polymers less than about 45K Daltons are particularly advantageous for rapid renal excretion. (Of course, in assessing the size of a polymer composition, it must be recognized that there will normally be a distribution of sizes actually present. The references to molecular weight of polymers herein generally refer to the molecular number weight, or $M_N$, i.e. the peak of this distribution.)

The following further clarifications are included to facilitate thorough understanding and interpretation of the disclosed teachings.

1. The preferred upper limit of about twelve nanometers, for either the sizes of the carriers or the overall sizes of the carrier-metal atom agents described above, relates to experimental observations that carriers (agents) which are smaller than this approximate size are most readily and rapidly transported across endothelial (or epithelial) barriers to which a subset of the present carriers will bind as a result of their complementarity to endothelial (epithelial) determinants. Such transport (and resulting tissue access) may occur by: a) induced (active) rapid transport across physically intact (nonporous) endothelium (or epithelium); b) passive extravasation through native or induced pores (usually in sites of disease or physically compromised endothelium (or epithelium)); or c) both "a" and "b" in varying ratios, depending on the physiopathologic state of the target tissues (organs).

One of the preferred molecular weight ranges of less than about 10,000 Daltons for carriers (or carrier-metal atom agents) is based on similar considerations, and also on the experimental observations that, following intravenous administration (or other routes leading to efficient intravenous uptake and circulation):

a) molecules larger than about 15,000 Daltons remain predominantly within the vascular compartment except in regions of altered vascular endothelium—chemical or physical (porosity) changes—and, hence, accumulate selectively in extravascular tissue sites based on disease-induced or organ-dependent endothelial (or epithelial) binding, transport and filtration; and b) molecules smaller than about 45,000 Daltons are cleared efficiently by the renal route. The more restricted, preferred molecular weight range for carriers of less than about 10,000-26,000 Daltons is based on: a) the observation that pharmaceutical heparins purified from beef-lung Fraction A sources tend to fall into this general molecular weight range; and b) experiments which indicate that carriers (or complete agents) in this lower molecular weight range may undergo the very most rapid transport out of the vascular (or epithelial) compartment into underlying (potentially otherwise sequestered) tissue sites and, hence, may accumulate most efficiently in the selected tissue target sites described above. (This does not exclude, however, that the slightly larger molecular species of 26,000-45,000 Daltons—or even larger ones—could be superior for selective localization under appropriate or specialized conditions.)

In an alternative class of embodiments, lower molecular weights (as low as 1,000 Daltons) may alternatively be used. In this class of embodiments, the composition would typically be designed to bind to circulating plasma substances, and thereby reformulate itself in the body as a functionally polymeric compound (adduct) greater than 15,000 Daltons. (Other uses of these low-MW versions may alternatively be indicated.)

2. In considering the polyatomic metal-atom complexes described above, the term "bridging ligands" extends to include both atoms and molecules and both organic and inorganic molecules. Thus, in heteropolyatomic metal-atom complexes, secondary metal atoms (paramagnetic or non-paramagnetic ones), as well as acetate, glycinate or other molecules, may serve as all or some of the bridging ligands for the primary (paramagnetic or therapeutic) metal atoms.

3. The weight ratios and molar ratios of (polyatomic) metal-atom complex-to-carrier substance are based on the following. Present examples teach that greater than about 35% (w/w) metal-atom complex-to-carrier can be achieved for $Cr_4S$-heparin, and even higher weight ratios are referenced as possible to achieve for hydrophilic microsphere-entrapped substrates. Hence an upper limit molar ratio of about 1:2 (or about 50% w/w) is referenced here. A lower limit molar ratio of about 1:25 (or about 5% w/w) derives from: a) present examples; b) the applicant's previous patent applications (referenced above); and, importantly, c) the requirement of at least about a 5% (w/w) content of polyatomic metal-atom complex in order to achieve sufficient superparamagnetic (strongly paramagnetic) tissue proton effects for tissue visualization of intravenously injected agent, and simultaneous avoidance of unacceptably large, acute plasma volume expansion due to osmotic effects of the macromolecular carriers. (Those skilled in the art will recognize that molar ratios and weight ratios are not directly equivalent, but vary with the molecular weights of the individual metal-atom complexes and polymeric carriers.)

4. For present purposes, the definition of "multiply paired-ion strong association" is as follows: "Two or more ionic charges each, of a positive and negative sign, located in close molecular proximity on the binding and bound groups, together with sufficient ionization of these charged groups at physiologic pH, to confer a chemical association which is sufficiently strong to give stable ion pairing in the presence of plasma or body fluids during localization and clearance of said metal-atom-carrier complexes (as elucidated in the preceding examples).

5. For the various metal atoms described above, it is emphasized here that numerous different metals may serve as either or both diagnostic or therapeutic agents (including $^{(195)}$platinum, gadolinium, boron, gold and others). Hence, they are included together in the present application, and are considered all to be variations of a single, unified approach to preparing compositions of matter involving (polyatomic or other) metal-atom-complex carriers. In terms of various pharmaceutical applications, platinum is used as a chemotherapeutic as well as potentially a paramagnetic agent for MRI diagnosis; and boron and boroleptics (boron complexes) can be used either as therapeutic radiation enhancers or as diagnostic agents, as can gold salts. Gold salts and metal-atom coordinates (including, among others, the therapeutic antiinflammatory/antiarthritic agent Auraofin TM ) can be administered for therapeutic purposes by formulating these salts (coordinates) as the metal-atom complexes described above. Hence, the single nature and structural category of these metal-atom-carrier compositions is apparent and supported in a fashion independent of their potentially multiple diagnostic and therapeutic pharmaceutical indications.

As will be recognized by those skilled in the art, the innovative concepts described in the present application can be modified and varied over a tremendous range of applications, and accordingly their scope is not limited except by the allowed claims.

What is claimed is:

1. A composition of matter for enhancing induced internal magnetic resonance images or shifting spectra arising from induced internal magnetic resonance signals, comprising:

a polyatomic complex comprising plural atoms having magnetic moments which are mutually magnetically coupled within the polyatomic complex, said complex including bridging molecular or atomic species which are individually bound to at least one of said plural atoms having magnetic moments and other atoms of the polyatomic complex, said polyatomic complex essentially of four Cr(III) atoms which are bound to a central tetrahedral sulfur atom and are octahedrally coordinated by bridging ligands, said bridging molecular species being free of intermolecular bonds; and a biocompatible, physiologically clearable carrier associated with the polyatomic complex, said carrier comprising heparin having a molecular weight between about 6,000 Daltons and 10,000 Daltons, and having binding complementarity to determinants of mammalian endothelia and epithelia, said carrier being in association with said polyatomic complex;

wherein the proportion of said polyatomic complex to said carrier is at least about 1:20 by weight; said carrier being of low toxicity to mammals and containing less than about 5 weight percent cross-linked or microaggregated species.

2. The composition of claim 1, wherein the heparin is beef-lung heparin.

3. The composition of claim 1, wherein the heparin is Fraction A heparin.

4. The composition of claim 1, wherein the heparin has a mean molecular weight of about 8,000.

5. A composition of matter for enhancing induced internal magnetic resonance images or shifting spectra arising from induced internal magnetic resonance signals, comprising:

a polyatomic complex comprising plural atoms having magnetic moments which are mutually magnetically coupled within the polyatomic complex, said complex including bridging molecular or atomic species which are individually bound to at least one of said plural atoms having magnetic moments and other atoms of the polyatomic complex, said polyatomic complex consisting essentially of four Cr(III) atoms which are bound to a central tetrahedral sulfur atom and are octahedrally coordinated by bridging ligands, said bridging molecular species being free of intermolecular bonds; and a biocompatible, physiologically clearable carrier associated with the polyatomic complex, said carrier comprising Fraction A of beef-lung heparin having a molecular weight between about 6,000 Daltons and 10,000 Daltons, and having binding complementarity to determinants of mammalian endothelia and epithelia; said carrier being in association with said polyatomic complex;

wherein the proportion of said polyatomic complex to said carrier is at least about 1:20 by weight; said carrier being of low toxicity to mammals and containing less than about 5 weight percent cross-linked or microaggregated species.

6. A composition of matter for enhancing induced internal magnetic resonance images or shifting spectra arising from induced internal magnetic resonance signals, comprising:

a polyatomic complex comprising plural atoms having magnetic moments which are mutually magnetically coupled within the polyatomic complex, said complex including bridging molecular or atomic species which are individually bound to at least one of said plural atoms having magnetic moments and other atoms of the polyatomic complex, said polyatomic complex consisting essentially of four Cr(III) atoms which are bound to a central tetrahedral sulfur atom and are octahedrally coordinated by bridging ligands, said bridging molecular species being free of intermolecular bonds; and a biocompatible, physiologically clearable carrier associated with the polyatomic complex, said carrier comprising Fraction A heparin or a fragment thereof having a molecular weight between about 1,000 Daltons and about 10,000 Daltons, and having binding complementarity to determinants of mammlian endothelia and epithelia; said carrier substance being in association with said polyatomic complex;

wherein the proportion of said polyatomic complex to said carrier is at least about 1:20 by weight and said carrier contains less than about 5 weight percent cross-linked or microaggregated species and being of low toxicity to mammals.

7. The composition of claim 1 wherein the carrier is in association by covalent bonding.

8. The composition of claim 1 wherein the heparin is native or modified.

9. The composition of claim 1 wherein said plural atoms include at least one of: chromium, copper, manganese, iron, platinum, cobalt, vanadium, molybdenum, tungsten, gadolinium, erbium dysprosium, europium and holmium.

10. The composition of claim 1 wherein said polyatomic complex has the formula $(Cr_4SR_nX_m)$, where R is a molecular species which is at least one of formate, formaldehyde, glutaraldehyde, acetate, glycinate, succinate, acetylacetonate, malonate, propionate, glutarate, hydroxamate, oxalate, 2-bromacetate, 2-sulfoethanoate, thiolacetate and thioglycolate; n is between 4 and 12; X is at least one of halide, sulfate, nitrate, carboxylate and phosphate stabilizing counterions; and m is between 1 and 2n.

11. The composition of claim 1 wherein the plural atoms having magnetic moments comprise Cr(III).

12. The composition of claim 1 wherein the polymeric complex comprises four Cr(III) atoms bound to a central tetrahedral sulfur atom and are octahedrally coordinated by bridging species.

13. The composition of claim 1, wherein said polyatomic complex comprises $Cr_4S(O_2CCH_3)_8(H_2O)_4^{+2}$.

14. The composition of claim 1 wherein said polyatomic complex is associated with said carrier noncovalently through a strong ionic, paired-ion, or charge interaction.

15. The composition of claim 14 wherein said strong interaction involves chemical coordination or chelation binding of said polyatomic complex to at least one reactive group of said carrier, each reactive group on said carrier, having a coordination number or ionic charge number between 2 and 10.

16. The composition of claim 1 wherein said polyatomic complex is covalently associated with said carrier.

17. The composition of claim 1 wherein said association is stabilized by physical or chemical means.

18. The composition of claim 17, wherein said association is stabilized by heating of a pre-dried polyatomic complex plus carrier combination to at least about 100 degrees Celsius in an organic solvent.

19. The composition of claim 18 wherein the organic solvent is acetone.

20. The composition of claim 18 wherein the organic solvent comprises a detergent or surfactant.

21. The composition of claim 18 wherein the organic solvent comprises between about 0.01% and about 25% detergent or surfactant by weight.

22. The composition of claim 18 wherein the organic solvent comprises a biocompatible oil.

23. The composition of claim 18 wherein the organic solvent comprises a polyol.

24. The composition of claim 23 wherein the polyol is polyethylene glycol.

25. The composition of claim 23 wherein the polyol is glycerol.

26. The composition of claim 17, wherein said association is stabilized by heating a pre-dried polyatomic complex and carrier combination to at least about 100 degrees Celsius in acetone, acetone comprising a polyosyethylene sorbitan mono-oleate detergent at between about 0.01 weight % and about 25 weight %, polyethylene glycol, glycerol or a biocompatible oil.

27. The composition of claim 1 wherein said polyatomic complex and said carrier are further formulated to produce nanoparticles between about 5 nanometers and about 99 nanometers in mean diameter.

28. The composition of claim 27 wherein said polyatomic complex is $Cr_4S(O_2CCH_3)_8(H_2O)_n$, where n is 1 to 4.

29. The composition of claim 5 wherein said polyatomic complex and carrier are further formulated to produce microparticles having a mean diameter between about 0.1 micrometers and about 15 micrometers, and said polyatomic complex is in association with a carrier comprising at least one of protamine, hexadimethrine, starch, and dextran, the heparin being at least a portion of microparticle surface.

30. The composition of claim 29 wherein said polyatomic complex is $Cr_4S(O_2CCH_3)_8(H_2O)_n$, where n is 1 to 4.

31. The composition of claim 1 wherein said polyatomic complex comprises $Cr_4S(O_2CCH_3)_8(H_2O)_n$, where n is between 1 and 4, and said carrier includes at least one of a dicarboxymethyl conjugate, succinate conjugate, ethylenediaminetetraacetate conjugate or diethylenetriaminepentaacetate conjugate of said heparin.

32. A composition of matter comprising a metal atom complex, said polyatomic complex consisting essentially of four Cr(III) atoms which are bound to a central tetrahedral sulfur atom and are octahedrally coordinated by bridging ligands, bound by chelation, coordination or multiply paired-ion strong association to a biocompatible, clearable carrier comprising native or modified Fraction A of beef-lung heparin having a molecular weight between about 1,000 Daltons and 10,000 Daltons, and having binding complementarity to determinants of mammalian endothelia and epithelia;

wherein said polyatomic complex and said carrier are in a weight ratio of at least about 1:20; and said carrier is nontoxic to mammals and contains less than about 5 weight percent cross-linked or microaggregated species.

33. A method for enhancing induced internal magnetic resonance images or shifting spectra arising from induced internal magnetic resonance signals, comprising the steps of:

identifying a living vertebrate animal to be imaged;

introducing into the blood stream or body cavity of said animal a diagnostic imaging or enhancing agent or spectral shift agent comprising a substantially completely water-soluble polymeric carrier molecule of native or modified Fraction A heparin or fragment thereof having a molecular weight range between about 1,000 Daltons and 10,000 Daltons, and having binding complementarity to determinants of mammalian endothelia and epithelia, said agent also comprising a polyatomic complex associated with said carrier molecule, said polyatomic complex including plural atoms of magnetic moment which are mutually magnetically coupled within the polyatomic complex said polyatomic complex essentially of four Cr(III) atoms which are bound to a central tetrahedral sulfur atom and are octahedrally coordinated by bridging ligands, applying to said animal a strong magnetic field which includes a magnetic gradient;

applying to at least a portion of said animal an electromagnetic perturbation field at a radio frequency generally corresponding to a resonant frequency of a predetermined atomic nucleus at a magnetic field strength which falls within the range of field strengths applied to said animal by said strong magnetic field; and measuring radio frequency emissions given off by magnetically aligned perturbed atomic nuclei, to determine a spatial map or spectral shift of magnetic resonance characteristics within tissues of said animal.

34. The composition of claim 1, 5 or 6 defined further as comprising a stabilizer.

35. The composition of claim 34 wherein the stabilizer is protamine.

36. The composition of claim 35 wherein the heparin and protamine are in a weight ratio between about 98:2 and 2:98.

37. The composition of claim 34 wherein the stabilizer is hexadimethrine.

38. The composition of claim 37 wherein the heparin and hexadimethrine are in a weight ratio of between about 98:2 and 2:98.

39. The composition of claim 34 wherein the stabilizer is starch.

40. The composition of claim 39 wherein the weight ratio of heparin to starch is between about 98:2 and 2:98.

* * * * *

UNITED STATES PATENT AND TRADEMARK OFFICE
CERTIFICATE OF CORRECTION

PATENT NO. : 5,213,788

DATED : May 25, 1993

INVENTOR(S) : Ranney

It is certified that error appears in the above-identified patent and that said Letters Patent is hereby corrected as shown below:

In claim 1, line 3, column 52, immediately after 'complex', insert --consisting--, therefor.

In claim 6, line 10, column 53, delete "mammlian" and insert --mammalian--, therefor.

In claim 9, line 25, column 53, immediately after 'erbium', insert a comma --,--, therefor.

In claim 10, line 32, column 53, delete "2-bromacetate" and insert --2-bromoacetate--, therefor.

In claim 26, lines 15 and 16, column 54, delete "polyosyethylene" and insert --polyoxyethylene--, therefor.

In claim 33, actual line 10, column 55, immediately after 'complex', insert a semicolon --;--, therefor.

In claim 33, actual line 11, column 55, immediately after 'complex', insert --consisting--, therefor.

Signed and Sealed this

Fourteenth Day of February, 1995

Attest:

BRUCE LEHMAN

Attesting Officer

Commissioner of Patents and Trademarks